United States Patent
Valmori et al.

(10) Patent No.: US 8,008,464 B2
(45) Date of Patent: Aug. 30, 2011

(54) SSX-4 PEPTIDES PRESENTED BY HLA CLASS II MOLECULES

(75) Inventors: Danila Valmori, Saint Herblain (FR); Maha Ayyoub, Saint Herblain (FR)

(73) Assignee: Ludwig Institute for Cancer Research Ltd., New York, NY (US)

( * ) Notice: Subject to any disclaimer, the term of this patent is extended or adjusted under 35 U.S.C. 154(b) by 0 days.

(21) Appl. No.: 12/960,878

(22) Filed: Dec. 6, 2010

(65) Prior Publication Data

US 2011/0091967 A1    Apr. 21, 2011

Related U.S. Application Data

(63) Continuation of application No. 10/936,888, filed on Sep. 9, 2004, now Pat. No. 7,858,743.

(51) Int. Cl.
C07H 21/04    (2006.01)

(52) U.S. Cl. .................................. 536/23.5; 435/320.1

(58) Field of Classification Search ........................ None
See application file for complete search history.

(56) References Cited

U.S. PATENT DOCUMENTS

| 5,965,535 A | 10/1999 | Chaux et al. |
| 6,291,658 B1 * | 9/2001 | Gure et al. ................ 536/23.1 |
| 6,548,064 B1 | 4/2003 | Tureci et al. |

FOREIGN PATENT DOCUMENTS

| WO | 50528 * | 11/1998 |
| WO | WO 02081646 A2 | 10/2002 |

OTHER PUBLICATIONS

Ayyoub, Maha, et al., CD4+ T Cell responses to SSX-4 in Melanoma Patients, *The Journal of Immunology*, Copyright 2005, The American Association of Immunologies, Inc., pp. 5092-5099.
Ayyoub, M. et al. 2004, An immunodominant SSX-2-derived epitope recognized by CD4+ T cells in association with HLA-DR, *J Clin Invest* 113: 1225-33.
Ayyoub, M et al., 2004, Identification of an SSX-2 epitope presented by dendritic cells to circulating autologous CD4+ T cells, *J. Immunol* 172:7206-7211.
Ayyoub, M. et al., 2002, Proteasome-assisted identification of a SSX-2-derived epitope recognized by tumor-reactive CTL infiltrating metastic melanoma, *J Immunol*, 168:1717-1722.
Ayyoub, M. et al., 2003, SSX antigens as tumor vaccine targets in human sarcoma, *Cancer Immunity*, 3:13.
Ayyoub, M. et al., 2003, Tumor-reactive SSX-2-specific CD8+ T cells are selectively expanded during immune responses to antigen expressing tumors in melanoma patients, *Cancer Res*, 63:5601-5606.
Ayyoub, M. et al., 2005, CD4+T cell responses to SSX-4 in melanoma patients, *J Immunol*, 174:5092-5099.
Brodin, B. et al., 2001, Cloning and characterization of spliced fusion transcript variants of synovial sarcoma: SYT/SSX4, SYT/SSX4v, and SYT/SSX2v. Possible regulatory role of the fusion gene product in wild type SYT expression, *Gene*, 268: 173-182.

Chaux, P. et al., 1999, Identification of MAGE-3 epitopes presented by HLA-DR molecules to cd4(+) T Lymphocytes, *J Exp Med*, 189:767-778.
Chen L. P. et al., 1991, Human Papillomavirus Type 16 Nucleoprotein E7 is a Tumor Rejection Antigen, *Proc. Natl. Acad. Sci USA* 88: 110-114.
Chen, C.H. et al., 2001, Expressions of cancer-testis antigens in human hepatocellular carcinomas, *Cancer Left*, 164: 189-195.
Chicz, R.M. et al., 1993, Specificity and promiscuity among naturally processed peptides bound to HLA-DR alleles, *J. Exp. Med.* 178:27-47.
Coulie; P.G. 1995, Antigens recognized on human tumors by cytolytic T lymphocytes; towards vaccination? *Stem Cells*, 13(4):393-403.
Crew, A.J. et al., 1995, Fusion of SYT to two genes, SSX1 and SSX2, encoding proteins with homology to the Kruppel-associated box in human synovial sarcoma, *Embo J*, 14:2333-2340.
De Smet, C. et al., 1996, The activation of human gene MAGE-1 in tumor cells is correlated with genome-wide demethylation, *Proc Natl Acad Sci U S A*, 93:7149-7153.
De Smet, C. et al., 2004, Promoter=dependent mechanism leading to selective hypomethylation within the 5' region of gene MAGE-A1 in tumor cells, *Mol Cell Biol*, 24(11):4781-4790.
Demoulin, J.B. et al., 1996, A single tyrosine of the interleukin-9 (IL-9) receptor is required for the STAT activation, antiapoptotic activity, and growth regulation by IL-9, *Mol. Cell, Biol.* 16(9):4710-4716.
Dos Santos, N.R. et al., 1997, Nuclear Localization of SYT, SSX and the synovial sarcoma-associated SYT-SSX fusion proteins, *Hum Mol Genet*, 6(9):1549-1558.
Dos Santos, N.R. et al., 2000, Heterogeneous expression of the SSX cancer/testis antigens in human melanoma lesions and cell lines, *Cancer Res*, 60:1654-1662.
Drakesmith, H. et al., 1998, In vivo priming of T cells against cryptic determinants by dendritic cells exposed to interleukin 6 and native antigen, *Proc Natl Acad U S A*, 95: 14903-14908.
Engelhard., V.H., 1994, Structure of peptides associated with class I and class II MHC molecules. *Annu. Rev. Immunol*, 12:181-201.
Gaschet, J. et al., 1996 Acute graft versus host disease due to T lymphocytes recognizing a single HLA-DPB1*0501 mismatch, *J Clin Invest*, 98:100-107.
Gilbert, S.C. et al., 1997, A protein particle vaccine containing multiple malaria epitomes, *Natural Biotechnol*. 15:1280-1284.
Gure, A.O. et al., 1997, SSX a multigene family with several members transcribed in normal testis and human cancer, *Int J Cancer*, 72:956-971.
Gure, A.O. et al., 2002, The SSX Gene Family: Characterization of 9 complete genes, *Int J Cancer*, 101:448-453.
Halder, T. et al., 1997, Isolation of novel HLA-DR restricted potential tumor-associated antigens from the melanoma cell line FM3, *Cancer Res*, 57:3238-3244.
Hung, K. et al., 1998, The central role of CD4(+) T cells in the Antitumor Immune Response, *J. Exp. Med.* 188(12):2357-2368.
James, R.F. et al., 1991, The effect of class II gene transfection on the tumourigenicity of the H-2K-negative mouse leukaemia cell line K36.16, *Immunology*, 72:213-218.

(Continued)

Primary Examiner — Sheela J Huff

(74) *Attorney, Agent, or Firm* — Wolf, Greenfield & Sacks, P.C.

(57) ABSTRACT

The invention describes HLA class II binding peptides encoded by the SSX-4 tumor associated gene, as well as nucleic acids encoding such peptides and antibodies relating thereto. The peptides stimulate the activity and proliferation of CD4+ T lymphocytes. Methods and products also are provided for diagnosing and treating conditions characterized by expression of the SSX-4 gene.

11 Claims, 6 Drawing Sheets

OTHER PUBLICATIONS

Kersh, G.J. et al., 2001, Structural and functional consequences of altering a peptide MGC anchor residue, *Journal of Immunology*, vol. 166, pp. 3345-3354.
Klebanoff, C.A. et al., 2004, IL-15 enhances the in vivo antitumor activity of tumor-reactive CD8+ T cells, *Proc. Natl. Acad. Sci. USA* 101(7):1969-74.
Klenerman, P. et al., 2002, Tracking T cells with tetramers; new tales from new tools, *Nat Rev Iummunol*, 2:263-272.
Kocher, T. et al., 1995, Identification and intracellular location of MAGE-3 gene product, *Cancer Res*, 55:2236-2239.
Li, Y. et al., 2006, Mutational analysis of the binding of staphylococcal enterotoxin D to the T cell receptor VB chain and major histocompatibility complex class II, *Immunology Letters*, vol. 105, pp. 55-60.
Lim, F.L. et al., 1998, A KRAB-related domain and a novel transcription repression domain in proteins encoded by SSX genes that are disrupted in human sarcomas, *Oncogene*, 17:2013-2018.
Margolin, J.F. et al., 1994, Kruppel-associated boxes are potent transcriptional repression domains, *Proc Natl Acad Sci U S A*, 91:4509-4513.
Mizushima, S. and Nagata, S., 1990, pEF-BOS, a powerful mammalian expression vector. *Nucleic Acids Res*, 18(17):5322.
Moosmann, P. et al., 1996, Transcriptional repression by RING finger protein TIF1 beta that interacts with the KRAB repressor domain of KOX1, *Nucleic Acids Res.*, 24:4859-4867.
Mumberg, D. et al., 1999, CD4(+) T cells eliminate MHC class II-negative cancer cells in vivo by indirect effects of IFN-gamma, *Proc Natl Acad Sci U S A*, 96; 8633-8638.
Murray K.J. et al., 1999, Age-specific effects of juvenile rheumatoid arthritis-associated HLA alleles, *Arthritis Rheum*, 42(9):1843-53.
Naka, N. et al., 2002, Expression of SSX genes in human osteosarcomas, *Int J Cancer*, 98:640-642.
Nanda, N.K and Sant, A.J., 2000, DM determines the cryptic and immunodominant fate of T cell epitopes, *J Exp Med*, 192(6):781-788.
Pieper, R. et al., 1999, Biochemical identification of mutated human melanoma antigen recognized by CD4(+)T cells, *J Exp Med*, 189(5):757-765.
Qin, Z. and Blankenstein, T., 2000, CD4+ T Cells—mediated tumor rejection involves inhibition of angiogenesis that is dependent on IFN gamma receptor expression by nonhematopoietic cells, *Immunity*, 12:677-686.
Rammensee H-G. et al., 1995, MHC ligands and peptide motifs: first listing, *Immunogenetics*, 41:178-228.
Rubio-Godoy, V. et al., 2002, Combinatorial peptide library-based identification of peptide ligands for tumor reactive cytolytic T lymphocytes of unknown specificity, *Eur Immunol*, 32:2292-2299.
Sanderson, S. et al., 1995, Expression of Endogenous peptide-Major Histocompatibility Complex Class II Complexes derived from Invariant Chain-Antigen Fusion Proteins, *Proc. Nat'l. Acad. Sci USA* 92:7217-7221.
Scanlan, M.J. et al., 2002, Cancer/testis antigens: an expanding family of targets for cancer immunotherapy, *Immunol Rev*, 188:22-32.
Schultz, E.S. et al., 2000, A MAGE-A3 peptide presented by HLA-DP4 is recognized on tumor cells by CD4+ cytolytic T lymphocytes, *Cancer Res*, 60:6272-6275.
Stratford-Perricaudet, L.D. et al., 1992, Widespread long-term gene transfer to mouse skeletal muscles and heart, *J. Clin. Invest.* 90:626-630.
Sturniolo, T. et al., 1999, Generation of tissue-specific and promiscuous HLA ligand databases using DNA microarrays and virtual HLA class II matrices, *Nat Biotechnol*, 17: 555-561.
Surman, s. et al., 2001, Localization of CD4+ T cell epitope hotspots to exposed strands of HIV envelope glycoprotein suggests structural influences on antigen processing, *Proc Natl Acad Sci U S A*, 98(8): 4587-4592.
Tam, J.P. et al., 1990, Incorporation of T and B epitopes of the circumsporzoite protein in chemically defined synthetic vaccine against malaria, *J. Exp. Med* 171 (1):299-306.
Thomson, S.A. et al., 1998, Targeting a polyepitope protein incorporating multiple class II-restricted viral epitopes to the secretory/endocytic pathway facilities immune recognition by CD4+ cytotoxic T lymphocytes: a novel approach to vaccine design, *J. Virol.* 72(3):2246-2252.
Thomson, S.A. et al., 1995, Minimal epitopes expressed in a recombinant polyepitope protein are processed and presented to CD8+ cytotoxic T cells: implications of vaccine design, *Proc. Natl. Acad. Sci. USA* 92:5845-5849.
Thomson, S.A. et al., 1996, Recombinant polyepitope vaccines for the delivery of multiple CD8 cytotoxic T cell epitopes, *J. Immunol.* 157(2):822-826.
Toes, E.E. et al., 1999, CD4 T cells and their role in antitumor immune responses, *J Exp Med*, 189(5):753-756.
Tureci,O. et al., 1996, The SSX-2 gene, which is involve in the t (X:18) translocation of synovial sarcomas, codes for the human tumor antigen HOM=MEL-40, *Cancer Res*, 56:4766-4772.
Tureci,O. et al., 1998, Expression of SSX genes in human tumors, *Int J Cancer*, 77: 19-23.
Viner, N.J. et al., 1995, Identification of a major I-EK-restricted determinant of hen egg lysozymes: limitations of lymph node proliferation studies in defining immunodominance and crypticity, *Proc Natl Acad Sci U S A*, 92:2214-2218.
Wang, R.F., 2001, The role of MHC class II-restricted tumor antigens and CD4+ T cells in antitumor immunity, *Trends Immunol*, 22:269-276.
Wang, R.F. et al., 1999, Cloning genes encoding MHC class II-restricted antigens; mutated CDC27 as a tumor antigen, *Science*, 282:1351-1354.
Wendtner, C.M. e al., 1997, Gene transfer of he costimulatory molecules B7-1 and B7-2 into human multiple myleoma cells by recombinant adeno=associated virus enhances the cytolytic T cell response, *Gene Ther.* 4:726-735.
Wu, T.C. e al., 1995, Engineering an Intracelluar Pathway for Major Histocompatibility Complex Class II Presented by Antigens, *Proc. Nat'l. Acad. Sci USA* 92:11671-11675.
Zeng, G. et al., 2001, CD4(+) T cell recognition of MHC class II-restricted epitopes from NY-ESO-1 presented by a prevalent HLA DP4 allele: association with NY-ESO-1 antibody production, *Proc Natl Acad Sci U S A*, 98:39-64-3969.
Zheng, P. et al., 1998, B7-CTLA4 interaction enhances both production of antitumor cytotoxic T lymphocytes and resistance to tumor challenge *Proc. Nat'l Acad. Sci. USA* 95:6284-6289.
Allsopp, C.E. et al., 1996, Comparison of numerous delivery systems for the induction of cytoxic T lymphocytes by immunization, *Eur. J. Immunol.* 26(8):1951-1959.
Altman, J.D. et al., 1996, Phenotypic analysis of antigen-specific T lymphocytes, *Science* 274:94-96.
Arnold, P.Y. et al. 2002, Reliable generation and use of MHC class II:gamma2aFc multimers for the identification of antigen-specific CD4(+) T cells, *J. Immunol. Methods* 271(1-2):137-151.
Bennett, S.R. et al., 1998, Help for cytotoxic-T cell responses is medicated by CD40 signalling, *Nature* 393:478-480.
Brett,D. et al., 1997, The SYT protein involved in the t(X;18) synovial sarcoma translocation is transcriptional activator localised in nuclear bodies, *Hum Mol Genet*, 6(9):1559-1564.
Brodin, B. et al., 2001, Cloning and characterization of spliced fusion transcript variants of synovial sarcoma: SYT/SSX4,SYT/SSX4v, and SYT/SSX2v. Possible regulatory role of the fusion gene product in wild type SYT expression, *Gene*, 262:173-182.
Calabresi, P. et al. Antineoplastic Agents, 1202-1263 Chapter 52, Rall, T.W., in Goodman and Gilman's "The Pharmacological basis of Therapeutics", 8th Ed., Taylor, P., Nies, A.S., Alfred Goodman Gilman, Eds., McGraw-Hill, 1990.
Clark, J. et al., 1994, Identification of novel genes, SYT and SSX, involved in the t(X;18)(p11.2;q11.2) translocation found in human synovial sarcoma, *Nat Genet*, 7:502-508.
Crawford, F. et al., 1998, Detection of antigen-specific T cells with multivalent soluble class II MHC covalent peptide complexes, *Immunity* 8:675-682.
De Bruijn, D.R. et al, 2002, The cancer-related protein SSX2 interacts with the human homologue of a Ras-like GTPase interactor, RAB3IP, and a novel nuclear protein, SSX21P, *Genes Chromosomes & Cancer*, 34:285-298.

De Leeuw, B. et al, 1996, A Novel Krüppel-associated box containing the SSX gene (SSX3) on the human X chromosome is not implicated in t(X:18)-positive synovial sarcomas, *Cytogenet Cell Genet*, 73: 179-183.

Dunbar, P.R. et al, 2002, Oligomeric MHC molecules and their homologues; state of the art, *J. Immunol. Methods* 268(1):3-7.

Dunbar, P.R. et al., 1998, Direct isolation, phenotyping and cloning of low-frequency antigen specific cytoxic T lymphocytes from peripheral blood, *Curr. Biol.* 8:413-416.

Fenton, R.G. et al., 1998, Induction of melanoma antigen-specific cytoxic T lymphocytes in vitro by stimulation with B7-expressing human melanoma cell lines, *J. Immunother.*, 21(2):95-108.

Gajewski, T. F. et al., 1995, Costimulation with B7-1, IL-6 and IL-12 is sufficient for primary generation of murine antitumor cytolytic T lymphocytes in vitro, *J. Immunol.* 154:5637-5648.

Glennie, M.J. et al, 2000, Clinical trials of antibody therapy, *Immunol Today*, 21:403-410.

Greenberg, P.D., 1991 Adoptive T cell therapy of tumors: mechanisms operative in the recognition and elimination of tumor cells, *Adv Immunol*, 49:281-355.

Hall, S.S., 1995, IL-12 at the crossroads, *Science* 268: 1432-1434.

Hugues, S. et al., 2002, Generation and use of alternative multimers of peptide/MHC complexes, *J. Immunological Meth.* 268: 83-92.

Hutloff, A et al., 1999, ICOS is an inducible T-cell co-stimulator structurally and functionally related to CD28, *Nature* 397:263-266.

Kim, J.J. et al., 1997 Engineering of in vivo immune responses to DNA immunization via codelivery of costimulatory molecule genes, *Nature Biotechnol.* 15:7:641-646.

Krieg, A.M. et al., 1995, CpG motifs in bacterial DNA trigger direct B-cell activation, *Nature* 374:546-9.

Kwok, W.W. et al., 2002, Use of class II tetramers for identification of CD4+ T cells, *J Immunol Methods*, 268:71-81.

Macbeath, G. et al, 2000, "Printing Proteins as Microarrays for High-Throughput Function Determination," *Science* 289: 1760-1763.

Nachman, R.J et al., 1995, Pseudodipeptide analogs of pyrokinin/PBAN (FXPRLa) insect neuropeptide family containing carbocyclic Pro-mimetic conformational components, *Regul, Pept.* 57:359-370.

Old, L.J., 1996 Immunotherapy for cancer, *Sci Am*, 275:136-143.

Parra, E et al., 1997, The role of B7-1 and LFA-3 in costimulation of CD8+T cells, *J Immunol.*, 158:637-642.

Rammensee, H. et al., 1999, SYFPEITHI: database for MHC ligands and peptide motifs, *Immunogenetics*, 50:213-219.

Ridge, J.P. et al., 1998, A conditioned dendritic cell can be a temporal bridge between a CD4+T helper and a T-killer cell, *Nature* 393; 474-478.

Sandberg, A.A. et al, 2002, Updates on the cytogenetics and molecular genetics of bone and soft tissue tumors. Synovial sarcoma, *Cancer Genet Cytogent*, 133:1-23.

Schoenberger, S.P. et al., 1998, T cell help for cytotoxic T lymphocytes is mediated by CD40-CD40L interactions, *Nature* 393:480-483.

Schultz-Thater, E. et al., 2000, NY-ESO-1 tumour associated antigen is a cytoplasmic protein detectable b specific monoclonal antibodies in cell lines and clinical specimens, *Br. J Cancer*, 83(2):204-208.

Sercarz, E.E. et al., 1993, Dominance and crypticity of T cell antigenic determinants, *Annu. Rev. Immunol.*, 11:729-766.

So, H.S. et al., 1997, Effect of a novel saponin adjuvant derived from *Quillaja saponaria* on the immune response to recombinant hepatitis B surface antigen, *Mol. Cells* 7:178-186.

Stephens, H.A.F. et al., 1995, The presence of HLA class II allele DPB1*0501 in ethnic Thais correlates with an enhanced vaccine-induced antibody response to a malaria sporozoite antigen, *Eur J Immunol*, 25:3142-3147.

Ulmer, J.B. et al., 1993, Heterologous protection against influenza by injection of DNA encoding a viral protein, *Science*, 259:1745-1749.

Wang Y.C. et al., 1996, Induction of autologous tumor-specific cytotoxic T-lymphocyte activity against a human renal carcinoma cell lime by B7-1 (CD8O) costimulation, *J Immunother Emphasis Tumor Immunol.*, 19(1):1-8.

Warnier, G. et al, 1996, Induction of a cytolytic T-cell response in mice with a recombinant adenovirus coding for tumor antigen P815A, *Int. J. Cancer*, 67:303-310.

* cited by examiner

SSX-4 PEPTIDES PRESENTED BY HLA CLASS II MOLECULES

RELATED APPLICATION

This application is a continuation of U.S. patent application Ser. No. 10/936,888, filed Sep. 9, 2004, the entire contents of which are incorporated herein by reference.

FIELD OF THE INVENTION

This invention relates to fragments of the tumor associated gene product SSX-4 which bind to and are presented to T lymphocytes by HLA class II molecules. The peptides, nucleic acid molecules which code for such peptides, as well as related antibodies and CD4$^+$ T lymphocytes, are useful, inter alia, in diagnostic and therapeutic contexts.

BACKGROUND OF THE INVENTION

The SSX genes are located on the X chromosome and encode a family of highly homologous nuclear proteins. Two family members, SSX-1 and SSX-2, were initially identified as fusion partners of the SYT gene in t(X;18)-positive synovial sarcomas (Clark, J., et al., 1994, Identification of novel genes, SYT and SSX, involved in the t(X;18)(p11.2;q11.2) translocation found in human synovial sarcoma, *Nat Genet*, 7:502-508; Crew, A. J., et al., 1995, Fusion of SYT to two genes, SSX1 and SSX2, encoding proteins with homology to the Kruppel-associated box in human synovial sarcoma, *Embo J*, 14:2333-2340). Later, serological analysis of tumor cDNA expression libraries (SEREX), revealed recognition of the SSX-2 encoded antigen by antibodies from cancer patients (Tureci, O. et al., 1996, The SSX-2 gene, which is involved in the t(X;18) translocation of synovial sarcomas, codes for the human tumor antigen HOM-MEL-40, *Cancer Res*, 56:4766-4772). Three additional homologous genes, SSX-3, -4 and -5, were identified (de Leeuw, B. et al., 1996, A novel Kruppel-associated box containing the SSX gene (SSX3) on the human X chromosome is not implicated in t(X;18)-positive synovial sarcomas, *Cytogenet Cell Genet*, 73:179-183; Gure, A. O. et al., 1997, SSX: a multigene family with several members transcribed in normal testis and human cancer, *Int J Cancer*, 72:965-971). Recently, SSX genes and pseudogenes have been further characterized, resulting in the definition of 9 (SSX-1 to -9) genes (Gure, A. O. et al., 2002, The SSX gene family: Characterization of 9 complete genes, *Int J Cancer*, 101:448-453). Similarly to other members of the cancer/testis antigens (CTA) group, to which the SSX gene family belongs, expression of the majority of the SSX genes, including SSX-1 to −5 and SSX-7, is restricted to gametogenic cells but silent in most adult normal tissues (Scanlan, M. J. et al., 2002, Cancer/testis antigens: an expanding family of targets for cancer immunotherapy, *Immunol Rev*, 188:22-32). Importantly, expression of these antigens is also detected in tumors of different histological types (Tureci, O. et al., 1998, Expression of SSX genes in human tumors, *Int J Cancer*, 77:19-23; Naka, N. et al., 2002, Expression of SSX genes in human osteosarcomas, *Int J Cancer*, 98:640-642; Chen, C. H., et al., 2001, Expressions of cancer-testis antigens in human hepatocellular carcinomas, *Cancer Lett*, 164:189-195; Ayyoub, M., et al., 2003, SSX antigens as tumor vaccine targets in human sarcoma, *Cancer Immunity*, 3:13). Therefore, antigens of the SSX family are targets of great interest for immunotherapy of cancer.

Among SSX genes, SSX-1, -2, -4 and -5 are the most commonly expressed. Several surveys of SSX gene expression in different human tumor types showed expression of several family members in a significant proportion of tumors, although at variable levels depending on the particular histological type. Expression of at least one SSX family member was frequently observed in tumor types such as head and neck cancer (75%), ovarian cancer (50%), malignant melanoma (43%) (Tureci, O. et al., 1998, Expression of SSX genes in human tumors, *Int J Cancer*, 77:19-23) and sarcoma (42%) (Naka, N. et al., 2002, Expression of SSX genes in human osteosarcomas, *Int J Cancer*, 98:640-642; Ayyoub, M., et al., 2003, SSX antigens as tumor vaccine targets in human sarcoma, *Cancer Immunity*, 3:13). We and others have previously reported that one antigen of the family, SSX-2, is naturally immunogenic in cancer patients bearing antigen-expressing tumors, and stimulates both specific humoral and T cell responses. Using tumor-reactive CD8$^+$ T lymphocytes from a melanoma patient we identified a CTL epitope restricted by the frequently expressed MHC class I allele HLA-A2 (Ayyoub, M., et al., 2002, Proteasome-assisted identification of a SSX-2-derived epitope recognized by tumor-reactive CTL infiltrating metastatic melanoma, *J Immunol*, 168:1717-1722; Rubio-Godoy, V., et al., 2002, Combinatorial peptide library-based identification of peptide ligands for tumor-reactive cytolytic T lymphocytes of unknown specificity, *Eur J Immunol*, 32:2292-2299). High affinity CD8$^+$ T cell responses to this epitope were specifically found in HLA-A2$^+$ melanoma patients bearing SSX-2 expressing tumors (Ayyoub, M., et al., 2003, Tumor-reactive SSX-2-specific CD8+ T cells are selectively expanded during immune responses to antigen expressing tumors in melanoma patients, *Cancer Res*, 63:5601-5606). More recently, we have reported the identification of three SSX-2 derived CD4$^+$ T cell epitopes recognized by specific T cells isolated from antigen expressing melanoma patients (Ayyoub, M., et al., 2004, Identification of an SSX-2 epitope presented by dendritic cells to circulating autologous CD4+ T cells, *J Immunol*, 172:7206-7211; Ayyoub, M., et al., 2004, An immunodominant SSX-2-derived epitope recognized by CD4+ T cells in association with HLA-DR, *J Clin Invest*, 113:1225-1233). No information, however, was thus far available on the immunogenicity of other SSX antigens.

Here, we report the analysis of naturally occurring CD4$^+$ T cell responses against another frequently expressed SSX antigen, SSX-4, in melanoma patients. Upon in vitro stimulation with a pool of long peptides spanning the protein sequence, we could detect and isolate SSX-4 specific CD4$^+$ T cells from 4/4 melanoma patients bearing antigen-expressing tumors but not from healthy individuals. From circulating CD4$^+$ T lymphocytes from these patients we isolated SSX-4 specific clonal CD4$^+$ T cell populations recognizing 7 distinct epitopes restricted by 5 different HLA class II alleles including some among the HLA-DR alleles more frequently expressed in several major ethnic groups. Interestingly, the majority of the identified epitopes were located within the Krüppel associated box (KRAB) repression domain in the N-terminal region of the protein. Together, the results of our study reveal a high spontaneous immunogenicity of SSX-4 and support the inclusion of this antigen in immunotherapy trials for melanoma and other SSX-expressing cancers.

SUMMARY OF THE INVENTION

It now has been discovered that the SSX-4 gene encodes HLA class II binding peptides that are epitopes presented by HLA-DR. These peptides, when presented by an antigen presenting cell having the appropriate HLA class II molecule, effectively induce the activation and proliferation of CD4+ T lymphocytes.

The invention provides isolated SSX-4 peptides which bind HLA class II molecules, and functional variants of such peptides. The functional variants contain one or more amino acid additions, substitutions or deletions to the SSX-4 peptide sequence. The invention also provides isolated nucleic acid molecules encoding such peptides, expression vectors containing those nucleic acid molecules, host cells transfected with those nucleic acid molecules, and antibodies to those peptides and complexes of the peptides and HLA class II antigen presenting molecules. T lymphocytes which recognize complexes of the peptides and HLA class II antigen presenting molecules are also provided. Kits and vaccine compositions containing the foregoing molecules additionally are provided. The foregoing can be used in the diagnosis or treatment of conditions characterized by the expression of SSX-4. As it is known that the members of the SSX family of polypeptides and nucleic acids share significant sequence identity and functional homology (e.g., as tumor antigens and precursors), the invention also embraces HLA binding peptides of similar amino acid sequence derived from members of the SSX family other than SSX-4. Therefore, it is understood that the disclosure contained herein of SSX-4 HLA class II binding peptides, compositions containing such peptides, and methods of identifying and using such peptides applies also to other members of the SSX tumor associated antigen family.

According to one aspect of the invention, isolated SSX-4 HLA class II-binding peptides are provided. The peptides include amino acid sequences set forth as SEQ ID NO:5, SEQ ID NO:6, SEQ ID NO:7, SEQ ID NO:8, SEQ ID NO:9 and SEQ ID NO:10, or a functional variant thereof comprising 1-5 amino acid substitutions. The HLA class II-binding peptide or functional variant does not include a full length SSX protein, particularly a full length SSX-4 protein. In certain embodiments, the isolated peptide comprises an amino acid sequence selected from the group consisting of SEQ ID NO:5, SEQ ID NO:6, SEQ ID NO:7, SEQ ID NO:8, SEQ ID NO:9 and SEQ ID NO:10. More preferably the isolated peptide consists of an amino acid sequence selected from the group consisting of SEQ ID NO:5, SEQ ID NO:6, SEQ ID NO:7, SEQ ID NO:8, SEQ ID NO:9 and SEQ ID NO:10.

In further embodiments, the isolated peptide includes an endosomal targeting signal, preferably including an endosomal targeting portion of human invariant chain Ii.

In other embodiments, the isolated peptide is non-hydrolyzable. Preferred non-hydrolyzable peptides include peptides comprising D-amino acids, peptides comprising a -psi[CH$_2$NH]-reduced amide peptide bond, peptides comprising a -psi[COCH$_2$]-ketomethylene peptide bond, peptides comprising a -psi[CH(CN)NH]-(cyanomethylene)amino peptide bond, peptides comprising a -psi[CH$_2$CH(OH)]-hydroxyethylene peptide bond, peptides comprising a -psi[CH$_2$O]-peptide bond, and peptides comprising a -psi[CH$_2$S]-thiomethylene peptide bond.

According to another aspect of the invention, compositions are provided that include an isolated HLA class I-binding peptide and an isolated SSX-4 HLA class II-binding peptide. The isolated SSX-4 HLA class II-binding peptide includes an amino acid sequence selected from the group set forth as SEQ ID NO:5, SEQ ID NO:6, SEQ ID NO:7, SEQ ID NO:8, SEQ ID NO:9 and SEQ ID NO:10, or a functional variant thereof comprising 1-5 amino acid substitutions (but not including the full length of a SSX protein, particularly a full length SSX-4 protein). Preferably the HLA class I-binding peptide and the SSX-4 HLA class II-binding peptide are combined as a polytope polypeptide.

In preferred embodiments, the isolated SSX-4 HLA class II-binding peptide includes an amino acid sequence selected from the group consisting of SEQ ID NO:5, SEQ ID NO:6, SEQ ID NO:7, SEQ ID NO:8, SEQ ID NO:9 and SEQ ID NO:10.

In further embodiments, the isolated SSX-4 HLA class II-binding peptide includes an endosomal targeting signal, preferably including an endosomal targeting portion of human invariant chain Ii.

According to a further aspect of the invention, compositions including one or more of the foregoing isolated SSX-4 HLA class II-binding peptides complexed with one or more isolated HLA class II molecules are provided. Preferably the number of isolated SSX-4 HLA class II-binding peptides and the number of isolated HLA class II molecules are equal. More preferably, the isolated SSX-4 HLA class II-binding peptides and the isolated HLA class II molecules are coupled as a tetrameric molecule of individual isolated SSX-4 HLA class II-binding peptides bound to individual isolated HLA class II molecules. Even more preferably, the HLA class II molecules are DR molecules.

According to still another aspect of the invention, isolated nucleic acid molecules are provided that encode the foregoing SSX-4 HLA class II-binding peptides, provided that the nucleic acid molecule does not encode a full length SSX protein, particularly a full length SSX-4 protein. Also provided are expression vectors including these isolated nucleic acid molecules operably linked to a promoter. In certain embodiments, the nucleic acid molecule includes a nucleotide sequence selected from the group consisting of SEQ ID NO:5, SEQ ID NO:6, SEQ ID NO:7, SEQ ID NO:8, SEQ ID NO:9 and SEQ ID NO:10. The foregoing expression vectors, in other embodiments, also include a nucleic acid molecule that encodes an HLA-DR molecule. Host cells transfected or transformed with the foregoing expression vectors also are provided; in some embodiments, the host cell expresses an HLA-DR molecule.

In another aspect of the invention, methods for selectively enriching a population of T lymphocytes with CD4+ T lymphocytes specific for a SSX-4 HLA class II-binding peptide are provided. The methods include contacting an isolated population of T lymphocytes with an agent presenting a complex of the SSX-4 HLA class II-binding peptide and an HLA class II molecule in an amount sufficient to selectively enrich the isolated population of T lymphocytes with the CD4+ T lymphocytes.

According to another aspect of the invention, methods for diagnosing a cancer characterized by expression of SSX-4 HLA class II-binding peptide are provided. The methods include contacting a biological sample isolated from a subject with an agent that is to specific for the SSX-4 HLA class II-binding peptide, and determining the interaction between the agent and the SSX-4 HLA class II-binding peptide as a determination of the disorder. Preferably the agent is an antibody or an antigen binding fragment thereof.

According to yet another aspect of the invention, methods for diagnosing a cancer characterized by expression of a SSX-4 HLA class II-binding peptide which forms a complex with an HLA class II molecule are provided. The methods include contacting a biological sample isolated from a subject with an agent that binds the complex, and determining binding between the complex and the agent as a determination of the disorder.

In still a further aspect of the invention, methods for treating a subject having a cancer characterized by expression of SSX-4 HLA class II-binding peptide are provided. The methods include administering to the subject an amount of a SSX-4 HLA class II-binding peptide effective to ameliorate the disorder.

According to a further aspect of the invention, additional methods for treating a subject having a cancer characterized by expression of SSX-4 HLA class II-binding peptide are provided. These methods include administering to the subject an amount of a HLA class I-binding peptide and an amount of a SSX-4 HLA class II-binding peptide effective to ameliorate the disorder. In some preferred embodiments, the HLA class I-binding peptide and the SSX-4 HLA class II-binding peptide are combined as a polytope polypeptide. Preferably the HLA class I-binding peptide is a SSX-4 HLA class I-binding peptide.

According to another aspect of the invention, methods for treating a subject having a cancer characterized by expression of SSX-4 are provided. The methods include administering to the subject an amount of a SSX-4 HLA class II-binding peptide effective to ameliorate the cancer.

In another aspect of the invention, methods are provided for treating a subject having a cancer characterized by expression of SSX-4 HLA class II-binding peptide. The methods include administering to the subject an amount of autologous CD4$^+$ T lymphocytes sufficient to ameliorate the disorder, wherein the CD4$^+$ T lymphocytes are specific for complexes of an HLA class II molecule and a SSX-4 HLA class II-binding peptide.

In the foregoing methods, the SSX-4 HLA class II-binding peptide preferably includes an amino acid sequence selected from the group set forth as SEQ ID NO:5, SEQ ID NO:6, SEQ ID NO:7, SEQ ID NO:8, SEQ ID NO:9 and SEQ ID NO:10, or a functional variant thereof comprising 1-5 amino acid substitutions. In certain preferred embodiments of the foregoing methods, the SSX-4 HLA class II-binding peptide includes an amino acid sequence selected from the group consisting of SEQ ID NO:5, SEQ ID NO:6, SEQ ID NO:7, SEQ ID NO:8, SEQ ID NO:9 and SEQ ID NO:10. In some embodiments, the HLA class II molecule is an HLA-DR molecule. In other embodiments, the SSX-4 HLA class II binding peptide includes an endosomal targeting signal, preferably an endosomal targeting portion of human invariant chain Ii.

In a further aspect of the invention, methods for identifying functional variants of a SSX-4 HLA class II-binding peptide are provided. The methods include selecting a SSX-4 HLA class II-binding peptide which includes an amino acid sequence selected from the group consisting of SEQ ID NO:5, SEQ ID NO:6, SEQ ID NO:7, SEQ ID NO:8, SEQ ID NO:9 and SEQ ID NO:10, an HLA class II-binding molecule which binds the SSX-4 HLA class II-binding peptide, and a T cell which is stimulated by the SSX-4 HLA class II-binding peptide presented by the HLA class II-binding molecule; mutating a first amino acid residue of the SSX-4 HLA class II-binding peptide to prepare a variant peptide; and determining the binding of the variant peptide to HLA class II-binding molecule and the stimulation of the T cell. Binding of the variant peptide to the HLA class II-binding molecule and stimulation of the T cell by the variant peptide presented by the HLA class II-binding molecule indicates that the variant peptide is a functional variant.

In some embodiments, the methods include a step of comparing the stimulation of the T cell by the SSX-4 HLA class II-binding peptide and the stimulation of the T cell by the functional variant as a determination of the effectiveness of the stimulation of the T cell by the functional variant.

According to another aspect of the invention, isolated polypeptides are provided that bind selectively the foregoing SSX-4 HLA class II-binding peptides, provided that the isolated polypeptide is not an HLA class II molecule. Also provided are isolated polypeptides that bind selectively a complex of the foregoing SSX-4 HLA class II-binding peptides and an HLA class II molecule, provided that the isolated polypeptide is not a T cell receptor. The foregoing isolated polypeptides preferably are antibodies, more preferably monoclonal antibodies. Preferred monoclonal antibodies include human antibodies, humanized antibodies, chimeric antibodies and single chain antibodies. In other embodiments, the isolated polypeptides are antibody fragments selected from the group consisting of Fab fragments, F(ab)$_2$ fragments, Fv fragments or fragments including a CDR3 region selective for a SSX-4 HLA class II-binding peptide.

The invention also provides isolated CD4$^+$ T lymphocytes that selectively bind a complex of an HLA class II molecule and a SSX-4 HLA class II-binding peptide, preferably wherein the HLA class II molecule is an HLA-DR molecule and wherein the SSX-4 HLA class II-binding peptide includes an amino acid sequence selected from the group set forth as SEQ ID NO:5, SEQ ID NO:6, SEQ ID NO:7, SEQ ID NO:8, SEQ ID NO:9 and SEQ ID NO:10, or a functional variant thereof. More preferably, the SSX-4 HLA class II-binding peptide includes an amino acid sequence selected from the group consisting of SEQ ID NO:5, SEQ ID NO:6, SEQ ID NO:7, SEQ ID NO:8, SEQ ID NO:9 and SEQ ID NO:10.

In a further aspect, the invention provides isolated antigen presenting cells that include a complex of an HLA class II molecule and a SSX-4 HLA class II-binding peptide, preferably wherein the HLA class II molecule is an HLA-DR molecule and wherein the SSX-4 HLA class II-binding peptide comprises an amino acid sequence selected from the group set forth as SEQ ID NO:5, SEQ ID NO:6, SEQ ID NO:7, SEQ ID NO:8, SEQ ID NO:9 and SEQ ID NO:10, or a functional variant thereof. More preferably, the SSX-4 HLA class II-binding peptide includes an amino acid sequence selected from the group consisting of SEQ ID NO:5, SEQ ID NO:6, SEQ ID NO:7, SEQ ID NO:8, SEQ ID NO:9 and SEQ ID NO:10.

According to another aspect of the invention, methods for identification of HLA class II-binding epitopes of a protein are provided. The methods include obtaining a peptide library of peptides that span the amino acid sequence of the protein; and contacting a population of cells containing CD4$^+$ T lymphocytes with the peptide library in the presence of antigen presenting cells to stimulate proliferation and/or cytokine production by CD4$^+$ T lymphocytes that selectively bind a peptide in the peptide library. The stimulation of CD4$^+$ T lymphocytes indicates that a peptide in the library contains at least one HLA class II epitope. In certain embodiments, the peptides are at least about 12 amino acids in length. In other embodiments, the peptides are between about 14 and about 50 amino acids in length. Preferably the peptides are between about 20 and about 22 amino acids in length.

In other embodiments, the peptides overlap each other by at least about 4 amino acids, more preferably by at least about 10 amino acids.

In still other embodiments, the antigen presenting cells are autologous peripheral blood mononuclear cells.

The method can include additional steps of screening the isolated CD4$^+$ T lymphocytes with submixtures or single peptides, and/or clonally expanding the stimulated CD4$^+$ T lymphocytes by periodic stimulation with the selected peptide and/or isolating the stimulated CD4+ T lymphocytes. In the last case, it is preferred that the isolation of the stimulated CD4+ T lymphocytes is carried out by cytokine guided flow cytometry cell sorting.

In some embodiments, the population of cells containing CD4+ T lymphocytes also includes CD8+ T lymphocytes. In these embodiments, the stimulation of both CD4+ and CD8+ T lymphocytes indicates that a peptide in the synthetic library contains both HLA class I and HLA class II epitopes.

The invention also provides pharmaceutical preparations containing any one or more of the medicaments described above or throughout the specification. Such pharmaceutical preparations can include pharmaceutically acceptable diluents, carriers and/or excipients.

The use of the foregoing compositions, peptides, cells and nucleic acids in the preparation of a medicament, particularly a medicament for treatment of cancer, or for treating an immune response is also provided.

These and other objects of the invention will be described in further detail in connection with the detailed description of the invention.

BRIEF DESCRIPTION OF THE SEQUENCES

Figure 1:
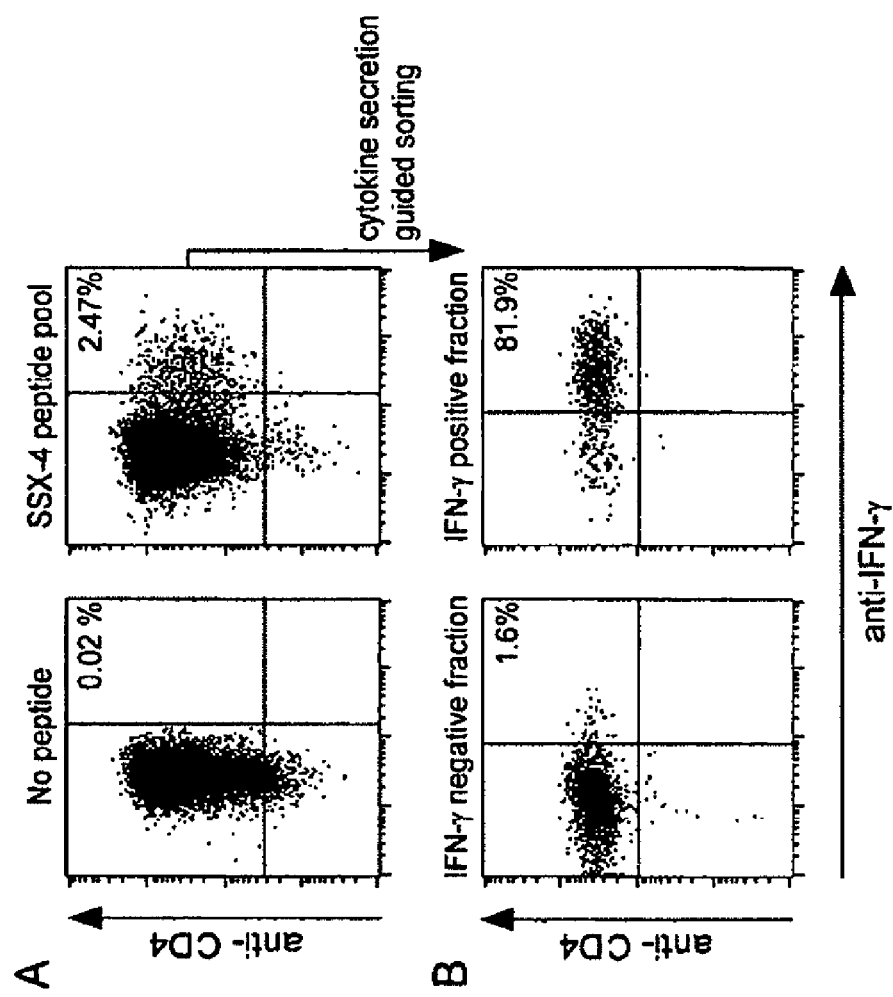
FIG. 1. Assessment of SSX-4 specific CD4+ T cell responses in circulating lymphocytes. A) The presence of specific CD4+ T cells in the cultures from melanoma patients and healthy donors (here shown for patient LAU 97) was assessed by intracellular staining with anti-IFN-γ specific mAb after incubation in the absence of antigen or after stimulation with a pool containing overlapping peptides spanning the SSX-4 protein, as indicated. Numbers in upper right quadrants are percent of cytokine producing cells among CD4+ T cells. B) IFN-γ secreting cells were isolated from the culture stimulated with the SSX-4 peptide pool by cytokine secretion guided magnetic sorting as detailed in the methods section.

SEQ ID NO:1 is the amino acid sequence of SSX-4 protein isoform a (NP_005627.1).
SEQ ID NO:2 is the nucleic acid sequence of SSX-4 transcript variant 1 (NM_005636).
SEQ ID NO:3 is the amino acid sequence of SSX-4 protein isoform b (NP_783856.1).
SEQ ID NO:4 is the nucleic acid sequence of SSX-4 transcript variant 2 (NM_175729).
SEQ ID NO:5 is the amino acid sequence of SSX-4 HLA class II binding peptide (31-50).
SEQ ID NO:6 is the amino acid sequence of SSX-4 HLA class II binding peptide (41-60).
SEQ ID NO:7 is the amino acid sequence of SSX-4 HLA class II binding peptide (51-70).
SEQ ID NO:8 is the amino acid sequence of SSX-4 HLA class II binding peptide (61-80).
SEQ ID NO:9 is the amino acid sequence of SSX-4 HLA class II binding peptide (101-120).
SEQ ID NO:10 is the amino acid sequence of SSX-4 HLA class II binding peptide (151-170).

DETAILED DESCRIPTION OF THE INVENTION

The invention provides isolated SSX-4 peptides presented by HLA class II molecules, which peptides stimulate the proliferation and activation of CD4+ T lymphocytes. Such peptides are referred to herein as "SSX-4 HLA class II binding peptides," "HLA class II binding peptides" and "MHC class II binding peptides." Hence, one aspect of the invention is an isolated peptide which includes the amino acid sequence of any one of SEQ ID NOs:5, 6, 7, 8, 9 and 10. The peptides referred to herein as "SSX-4 HLA class II binding peptides" include fragments of SSX-4 protein, but do not include full-length SSX-4 protein (e.g., SEQ ID NOs:1 or 3). Likewise, nucleic acids that encode the "SSX-4 HLA class II binding peptides" include fragments of the SSX-4 gene coding region, but do not include the full-length SSX-4 coding region (e.g., as found in SEQ ID NOs:2 or 4). Fragments may include fragments of either SSX-4 isoform a (e.g. as set forth in SEQ ID NO:1) or SSX-4 isoform b (e.g. as set forth in SEQ ID NO:3).

The examples below show the isolation of peptides which are SSX-4 HLA class II binding peptides. These exemplary peptides are processed translation products of an SSX-4 nucleic acid (e.g., SEQ ID NOs:2 or 4; the encoded polypeptide sequences are given as SEQ ID NOs:1 or 3). As such, it will be appreciated by one of ordinary skill in the art that the translation products from which a SSX-4 HLA class II binding peptide is processed to a final form for presentation may be of any length or sequence so long as they encompass the SSX-4 HLA class II binding peptide. Peptides or proteins as small as 20 amino acids and as large as the amino acid sequence of a SSX-4 protein (SEQ ID NOs:1 and 3) are appropriately processed, presented by HLA class II molecules and effective in stimulating CD4+ T lymphocytes. SSX-4 HLA class II binding peptides, such as the peptides of SEQ ID NO:5, SEQ ID NO:6, SEQ ID NO:7, SEQ ID NO:8, SEQ ID NO:9 and SEQ ID NO:10 may have one, two, three, four, five, six, seven, eight, nine, ten, 15, 20, 25, 30, 40, 50 or more amino acids added to either or both ends. The antigenic portion of such a peptide is cleaved out under physiological conditions for presentation by HLA class II molecules. It is also well known in the art that HLA class II peptide length is variable between about 10 amino acids and about 30 amino acids (Engelhard, *Ann. Rev. Immunol.* 12:181-201, 1994). Most of the HLA class II binding peptides fall in to the length range of 12-20 amino acids. Nested sets of HLA class II binding peptides have been identified, wherein the peptides share a core sequence but have different amino acids at amino and/or carboxyl terminal ends (see, e.g., Chicz et al., *J. Exp. Med.* 178:27-47, 1993). Thus additional SSX-4 HLA class II binding peptides comprising at least a portion of the sequences of the peptides reported herein, as well as homologous SSX family HLA class II binding peptides (e.g., of similar sequence from other SSX proteins such as SSX-1, SSX-2 and SSX-3), can be identified by one of ordinary skill in the art according to the procedures described herein.

The procedures described in the Examples that were utilized to identify SSX-4 HLA class II binding peptides also can be utilized to identify other HLA class II binding peptides, including homologous SSX family HLA class II binding peptides. Thus, for example, one can load antigen presenting cells, such as dendritic cells of normal blood donors, with a recombinant SSX protein (or a number of overlapping peptide fragments thereof as is described herein) by contacting the cells with the SSX polypeptide (or a series of peptides) or by introducing into the cells a nucleic acid molecule which directs the expression of the SSX protein (or peptide) of interest. The antigen-presenting cells then can be used to induce in vitro the activation and/or proliferation of specific CD4 lymphocytes that recognize SSX HLA class II binding peptides. The CD4 lymphocytes can be isolated according to standard methods, including cytokine guided flow cytometry cell sorting as described herein.

The sequence of the peptide epitope then can be determined as described in the Examples, e.g., by stimulating cells with peptide fragments of the SSX protein used to stimulate the activation and/or proliferation of CD4 lymphocytes. SSX-4 epitopes that are efficiently processed from SSX-4 protein administered exogenously or synthesized endogenously and presented to specific CD4+ T cells are preferred. If a peptide library is used in the initial screening, then subsets of these peptides or individual peptides can be used for the subsequent screening. Preferably the peptides are at least about 12 amino acids in length for efficient binding to HLA class II molecules. More preferably, the peptides are between about 14 and about 50 amino acids in length, still more preferably between about 20 and about 22 amino acids in length. By using overlapping peptides, all possible epitopes can be screened. In some embodiments, the peptides overlap each other by at least about 4 amino acids, but preferably the peptides overlap each other by at least about 10 amino acids.

In addition, one can make predictions of peptide sequences derived from SSX family proteins which are candidate HLA class II binding peptides based on the consensus amino acid sequences for binding HLA class II molecules. Peptides which are thus selected can be used in the assays described herein for inducing activation and/or proliferation of specific CD4 lymphocytes and identification of peptides. Additional methods of selecting and testing peptides for HLA class II binding are well known in the art. The foregoing methods also can be used to simultaneously screen a protein sequence for the presence of both HLA class I and HLA class II epitopes by contacting the antigen presenting cells with a population of cells that contains both CD4+ T lymphocytes and CD8+ T lymphocytes. The stimulation of both CD4+ and CD8+ T lymphocytes indicates that a peptide in the synthetic library contains both HLA class I and HLA class II epitopes. Stimulation of CD8+ or CD4+ T lymphocytes indicates that only HLA class I or HLA class II epitopes exist in a reactive peptide.

As noted above, the invention embraces functional variants of SSX-4 HLA class II binding peptides. As used herein, a "functional variant" or "variant" of a HLA class II binding peptide is a peptide which contains one or more modifications to the primary amino acid sequence of a HLA class II binding peptide and retains the HLA class II and T cell receptor binding properties disclosed herein. Modifications which create a SSX-4 HLA class II binding peptide functional variant can be made for example 1) to enhance a property of a SSX-4 HLA class II binding peptide, such as peptide stability in an expression system or the stability of protein-protein binding such as HLA-peptide binding; 2) to provide a novel activity or property to a SSX-4 HLA class II binding peptide, such as addition of an antigenic epitope or addition of a detectable moiety; or 3) to provide a different amino acid sequence that produces the same or similar T cell stimulatory properties. Modifications to SSX-4 (as well as SSX family) HLA class II binding peptides can be made to nucleic acids which encode the peptide, and can include deletions, point mutations, truncations, amino acid substitutions and additions of amino acids. Alternatively, modifications can be made directly to the polypeptide, such as by cleavage, addition of a linker molecule, addition of a detectable moiety, such as biotin, addition of a fatty acid, substitution of one amino acid for another and the like.

Preferably the substitutions are not made at anchor residues of a MHC binding epitope. For example, for HLA-DRB1*0301, the anchor residues are at relative position 1 (L, I, F, M, or V); relative position 4 (D), relative position 6 (K, R, E, Q, or N), and relative position 9 (Y, L, or F) (Rammensee, H-G. et al., 1995, Immunogenetics, 41:178-228; Steven, G. E., et al., The HLA Facts Book, Academic Press, 2000). Anchor residues of other MHC binding epitopes are well known in the art; see for example, the website of the European Bioinformatics Institute, Immunogenetics database.

Variants also can be selected from libraries of peptides, which can be random peptides or peptides based on the sequence of the SSX peptides including substitutions at one or more positions (preferably 1-5). For example, a peptide library can be used in competition assays with complexes of SSX peptides bound to HLA class II molecules (e.g. dendritic cells loaded with SSX peptide). Peptides which compete for binding of the SSX peptide to the HLA class II molecule can be sequenced and used in other assays (e.g. CD4 lymphocyte proliferation) to determine suitability as SSX peptide functional variants.

Modifications also embrace fusion proteins comprising all or part of a SSX HLA class II binding peptide amino acid sequence, such as the invariant chain-SSX-4 fusion proteins described herein. The invention thus embraces fusion proteins comprising SSX-4 HLA class II binding peptides and endosomal targeting signals such as the human invariant chain (Ii). An "endosomal targeting portion" of the human invariant chain or other targeting polypeptide is that portion of the molecule which, when fused or conjugated to a second polypeptide, increases endosomal localization of the second polypeptide. Thus endosomal targeting to portions can include the entire sequence or only a small portion of a targeting polypeptide such as human invariant chain Ii. One of ordinary skill in the art can readily determine an endosomal targeting portion of a targeting molecule.

Prior investigations (PCT/US99/21230) noted that fusion of an endosomal targeting portion of LAMP-1 protein did not significantly increase targeting of MAGE-A3 to the HLA class II peptide presentation pathway. It is possible that this was a MAGE-A3 specific effect. Therefore, the SSX-4 peptides of the invention can be tested as fusions with LAMP-1 to determine if such fusion proteins are efficiently targeted to the HLA class II peptide presentation pathway. Additional endosomal targeting signals can be identified by one of ordinary skill in the art, fused to SSX-4 or a SSX-4 HLA class II binding portion thereof, and tested for targeting to the HLA class II peptide presentation pathway using no more than routine experimentation.

The amino acid sequence of SSX HLA class II binding peptides may be of natural or non-natural origin, that is, they may comprise a natural SSX HLA class II binding peptide molecule or may comprise a modified sequence as long as the amino acid sequence retains the ability to stimulate helper T cells when presented and retains the property of binding to an HLA class II molecule such as an HLA DR molecule. For example, SSX-4 HLA class II binding peptides in this context may be fusion proteins including a SSX-4 HLA class II binding peptide and unrelated amino acid sequences, synthetic SSX-4 HLA class II binding peptides, labeled peptides, peptides isolated from patients with a SSX-4 expressing cancer, peptides isolated from cultured cells which express SSX-4, peptides coupled to nonpeptide molecules (for example in certain drug delivery systems) and other molecules which include the amino acid sequence of SEQ ID NOs: 5, 6, 7, 8, 9 and 10.

Preferably, the SSX-4 HLA class II binding peptides are non-hydrolyzable. To provide such peptides, one may select SSX-4 HLA class II binding peptides from a library of non-hydrolyzable peptides, such as peptides containing one or more D-amino acids or peptides containing one or more non-hydrolyzable peptide bonds linking amino acids. Alternatively, one can select peptides which are optimal for inducing CD4$^+$ T lymphocytes and then modify such peptides as necessary to reduce the potential for hydrolysis by proteases. For example, to determine the susceptibility to proteolytic cleavage, peptides may be labeled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of a SSX-4 HLA class II binding peptide with the known cleavage site specificity of a panel of proteases. Based on the results of such assays, individual peptide bonds which are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include, but are not limited to, -psi[CH$_2$NH]— reduced amide peptide bonds, -psi[COCH$_2$]— ketomethylene peptide bonds, -psi[CH(CN)NH]— (cyanomethylene)amino peptide bonds, -psi[CH$_2$CH(OH)]— hydroxyethylene peptide bonds, -psi[CH$_2$O]— peptide bonds, and -psi[CH$_2$S]— thiomethylene peptide bonds.

Nonpeptide analogs of peptides, e.g., those which provide a stabilized structure or lessened biodegradation, are also contemplated. Peptide mimetic analogs can be prepared based on a selected SSX-4 HLA class II binding peptide by replacement of one or more residues by nonpeptide moieties. Preferably, the nonpeptide moieties permit the peptide to retain its natural conformation, or stabilize a preferred, e.g., bioactive, confirmation. Such peptides can be tested in molecular or cell-based binding assays to assess the effect of the substitution(s) on conformation and/or activity. One example of methods for preparation of nonpeptide mimetic analogs from peptides is described in Nachman et al., *Regul. Pept.* 57:359-370 (1995). Peptide as used herein embraces all of the foregoing.

If a variant involves a change to an amino acid of SEQ ID NOs: 5, 6, 7, 8, 9 and 10 functional variants of the SSX-4 HLA class II binding peptide having conservative amino acid substitutions typically will be preferred, i.e., substitutions which retain a property of the original amino acid such as charge, hydrophobicity, conformation, etc. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Other methods for identifying functional variants of the SSX-4 HLA class II binding peptides are provided in a published PCT application of Strominger and Wucherpfennig (PCT/US96/03182). These methods rely upon the development of amino acid sequence motifs to which potential epitopes may be compared. Each motif describes a finite set of amino acid sequences in which the residues at each (relative) position may be (a) restricted to a single residue, (b) allowed to vary amongst a restricted set of residues, or (c) allowed to vary amongst all possible residues. For example, a motif might specify that the residue at a first position may be any one of the residues valine, leucine, isoleucine, methionine, or phenylalanine; that the residue at the second position must be histidine; that the residue at the third position may be any amino acid residue; that the residue at the fourth position may be any one of the residues valine, leucine, isoleucine, methionine, phenylalanine, tyrosine or tryptophan; and that the residue at the fifth position must be lysine.

Other computational methods for selecting amino acid substitutions, such as iterative computer structural modeling, can also be performed by one of ordinary skill in the art to prepare variants. Sequence motifs for SSX-4 HLA class II binding peptide functional variants can be developed by analysis of the binding domains or binding pockets of major histocompatibility complex HLA-DR proteins and/or the T cell receptor ("TCR") contact points of the SSX-4 HLA class II binding peptides disclosed herein. By providing a detailed structural analysis of the residues involved in forming the HLA class II binding pockets, one is enabled to make predictions of sequence motifs for binding of SSX peptides to any of the HLA class II proteins.

Using these sequence motifs as search, evaluation, or design criteria, one is enabled to identify classes of peptides (e.g. SSX HLA class II binding peptides, particularly the SSX-4 peptides disclosed herein, and functional variants thereof) which have a reasonable likelihood of binding to a particular HLA molecule and of interacting with a T cell receptor to induce T cell response. These peptides can be synthesized and tested for activity as described herein. Use of these motifs, as opposed to pure sequence homology (which excludes many peptides which are antigenically similar but quite distinct in sequence) or sequence homology with unlimited "conservative" substitutions (which admits many peptides which differ at critical highly conserved sites), represents a method by which one of ordinary skill in the art can evaluate peptides for potential application in the treatment of disease.

The Strominger and Wucherpfennig PCT application, and references cited therein, all of which are incorporated by reference, describe the HLA class II and TCR binding pockets which contact residues of an HLA class II peptide. By keeping the residues which are likely to bind in the HLA class II and/or TCR binding pockets constant or permitting only specified substitutions, functional variants of SSX HLA class II binding peptides can be prepared which retain binding to HLA class II and T cell receptor.

Thus methods for identifying additional SSX family HLA class II peptides, in particular SSX-4 HLA class II binding peptides, and functional variants thereof, are provided. In general, any SSX protein can be subjected to the analysis noted above, peptide sequences selected and the tested as described herein. With respect to SSX-4, for example, the methods include selecting a SSX-4 HLA class II binding peptide, an HLA class II binding molecule which binds the SSX-4 HLA class II binding peptide, and a T cell which is stimulated by the SSX-4 HLA class II binding peptide presented by the HLA class II binding molecule. In preferred embodiments, the SSX-4 HLA class II binding peptide comprises the amino acid sequence of SEQ ID NOs: 5, 6, 7, 8, 9 and 10. More preferably, the peptide consists essentially of or consists of the amino acid sequences of SEQ ID NOs: 5, 6, 7, 8, 9 and 10. The first amino acid residue of the SSX-4 HLA class II binding peptide is mutated to prepare a variant peptide. The amino acid residue can be mutated according to the principles of HLA and T cell receptor contact points set forth in the Strominger and Wucherpfennig PCT application described above. Any method for preparing variant peptides can be employed, such as synthesis of the variant peptide, recombinantly producing the variant peptide using a mutated nucleic acid molecule, and the like.

The binding of the variant peptide to HLA class II binding molecules and stimulation of the T cell are then determined according to standard procedures. For example, as exemplified below, the variant peptide can be contacted with an antigen presenting cell which contains the HLA class II molecule which binds the SSX-4 peptide to form a complex of the variant peptide and antigen presenting cell. This complex can then be contacted with a T cell which recognizes the SSX-4 HLA class II binding peptide presented by the HLA class II binding molecule. T cells can be obtained from a patient having a condition characterized by expression of SSX-4, such as cancer. Recognition of variant peptides by the T cells can be determined by measuring an indicator of T cell stimulation such as cytokine production (e.g., TNF or IFN-γ) or proliferation of the T cells. Similar procedures can be carried out for identification and characterization of other SSX family HLA class II binding peptides.

Binding of a variant peptide to the HLA class II binding molecule and stimulation of the T cell by the variant peptide presented by the HLA class II binding molecule indicates that the variant peptide is a functional variant. The methods also can include the step of comparing the stimulation of the T cell by the SSX-4 HLA class II binding peptide and the stimulation of the T cell by the functional variant as a determination of the effectiveness of to the stimulation of the T cell by the functional variant. By comparing the functional variant with the SSX-4 HLA class II binding peptide, peptides with increased T cell stimulatory properties can be prepared.

The foregoing methods can be repeated sequentially with a second, third, fourth, fifth, sixth, seventh, eighth, ninth, and tenth substitutions to prepare additional functional variants of the disclosed SSX-4 HLA class II binding peptides.

Variants of the SSX-4 HLA class II binding peptides prepared by any of the foregoing methods can be sequenced, if necessary, to determine the amino acid sequence and thus deduce the nucleotide sequence which encodes such variants.

Also a part of the invention are those nucleic acid sequences which code for a SSX HLA class II binding peptides or variants thereof and other nucleic acid sequences which hybridize to a nucleic acid molecule consisting of the above described nucleotide sequences, under high stringency conditions. Preferred nucleic acid molecules include those comprising the nucleotide sequences that encode SEQ ID NOs: 5, 6, 7, 8, 9 and 10, e.g. SEQ ID NOs:2 or 4. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, high stringency conditions, as used herein, refers to hybridization at 65° C. in hybridization buffer (3.5×SSC, 0.02% Ficoll, 0.02% Polyvinyl pyrolidone, 0.02% Bovine Serum Albumin, 25 mM $NaH_2PO_4$ (pH7), 0.5% SDS, 2 mM EDTA). SSC is 0.15M Sodium Chloride/0.015M Sodium Citrate, pH 7; SDS is Sodium Dodecyl Sulphate; and EDTA is Ethylene diaminetetraacetic acid. After hybridization, the membrane upon which the DNA is transferred is washed at 2×SSC at room temperature and then at 0.1-0.5×SSC/0.1×SDS at temperatures up to 68° C., e.g., 55° C., 60° C., 65° C. or 68° C. Alternatively, high stringency hybridization may be performed using a commercially available hybridization buffer, such as ExpressHyb™ buffer (Clontech) using hybridization and washing conditions described by the manufacturer.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids encoding the SSX HLA class II binding peptides of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 75% nucleotide identity and/or at least 90% amino acid identity to the nucleic acids that encode a SSX-4 HLA class II binding peptide (such as SEQ ID NOs: 5, 6, 7, 8, 9 and 10) or to the amino acid sequence of such a peptide, respectively. In some instances homologs and alleles will share at least 90% nucleotide identity and/or at least 95% amino acid identity, in other embodiments homologs and alleles will share at least 95% nucleotide identity and/or at least 98% amino acid identity, in further embodiments homologs and alleles will share at least 97% nucleotide identity and/or at least 99% amino acid identity and in still other instances will share at least 99% nucleotide identity and/or at least 99.5% amino acid identity. Complements of the foregoing nucleic acids also are embraced by the invention.

In screening for nucleic acids which encode a SSX HLA class II binding peptide, a nucleic acid hybridization such as a Southern blot or a Northern blot may be performed using the foregoing conditions, together with a detectably labeled probe (e.g., radioactive such as $^{32}$P, chemiluminescent, fluorescent labels). After washing the membrane to which DNA encoding a SSX HLA class II binding peptide was finally transferred, the membrane can be placed against X-ray film, phosphorimager or other detection device to detect the detectable label.

The invention also includes the use of nucleic acid sequences which include alternative codons that encode the same amino acid residues of the SSX HLA class II binding peptides. For example, as disclosed herein, the peptide YFSKKEWEKMKSSEKIVYVY (SEQ ID NO:5) is a SSX-4 HLA class II binding peptide. The lysine residues (amino acids No. 4, 5, 9, 11 and 15 of SEQ ID NO:5) can be encoded by the codons AAA, and AAG. Each of the two codons is equivalent for the purposes of encoding a lysine residue. Thus, it will be apparent to one of ordinary skill in the art that any of the lysine-encoding nucleotide triplets may be employed to direct the protein synthesis apparatus, in vitro or in vivo, to incorporate a lysine residue. Similarly, nucleotide sequence triplets which encode other amino acid residues comprising the SSX-4 HLA class II binding peptide of SEQ ID NO:5 include: GUA, GUC, GUG and GUU (valine codons); GAA and GAG (glutamine codons); UUC and UUU (phenylalanine codons) and UAC and UAU (tyrosine codons). Other amino acid residues may be encoded similarly by multiple nucleotide sequences. Thus, the invention embraces degenerate nucleic acids that differ from the native SSX HLA class II binding peptide encoding nucleic acids in codon sequence due to the degeneracy of the genetic code.

It will also be understood that the invention embraces the use of the sequences in expression vectors, as well as to transfect host cells and cell lines, be these prokaryotic (e.g., E. coli), or eukaryotic (e.g., dendritic cells, CHO cells, COS cells, yeast expression systems and recombinant baculovirus expression in insect cells). The expression vectors require that the pertinent sequence, i.e., those described supra, be operably linked to a promoter. As it has been found that human HLA-DR molecules present a SSX-4 HLA class II binding peptide, the expression vector may also include a nucleic acid sequence coding for a HLA-DR molecule. In a situation where the vector contains both coding sequences, it can be used to transfect a cell which does not normally express either one. The SSX-4 HLA class II binding peptide coding sequence may be used alone, when, e.g. the host cell already expresses a HLA-DR molecule, as appropriate for the peptide. Of course, there is no limit on the particular host cell which can be used as the vectors which contain the two coding sequences may be used in host cells which do not express HLA-DR molecules if desired, and the nucleic acid coding for the SSX-4 HLA class II binding peptide can be used in antigen presenting cells which express a HLA-DR molecule.

As described herein, SSX-4 HLA class II binding peptides bind to HLA class II molecules, preferably HLA-DR molecules. As used herein, "an HLA-DR molecule" includes, but is not limited to, the preferred subtypes DRB1 *0101, *0301, *0701, *1001, *1101, *1302 and *1501, DRB3*0202 and *0301, and DRB5*0101, including: DRB1*010101, DRB1*010102, DRB1*030101, DRB1*030102, DRB1*070101, DRB1*070102, DRB1*110101, DRB1*110102, DRB1*110103, DRB1*110104, DRB1*110105, DRB1*130201, DRB1*130202, DRB1*150101, DRB1*150102, DRB1*150103, DRB1*150104, DRB1*150105, DRB3*020201, DRB3*020202, DRB3*020203, DRB3*020204, DRB3*030101, DRB3*030102, DRB5*010101, DRB5*010102, DP10, and other subtypes known to one of ordinary skill in the art. Other subtypes, including those related to DRB1 *0101, *0301, *0701, *1101, *1302 and *1501, DRB3*0202 and *0301, and DRB5*0101 can be found in various publications and internet resources that update HLA allele lists.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate autonomously or after integration into the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

Preferably the expression vectors contain sequences which target a SSX family polypeptide, e.g. SSX-4, or a HLA class II binding peptide derived therefrom, to the endosomes of a cell in which the protein or peptide is expressed. HLA class II molecules contain an invariant chain (Ii) which impedes binding of other molecules to the HLA class II molecules. This invariant chain is cleaved in endosomes, thereby permitting binding of peptides by HLA class II molecules. Therefore in a preferred embodiment, the SSX-4 HLA class II binding peptides and precursors thereof (e.g. the SSX-4 protein) are targeted to the endosome, thereby enhancing the binding of SSX-4 HLA class II binding peptide to HLA class II molecules. Targeting signals for directing molecules to endosomes are known in the art and these signals conveniently can be incorporated in expression vectors such that fusion proteins which contain the endosomal targeting signal are produced. Sanderson et al. (Proc. Nat'l. Acad. Sci. USA 92:7217-7221, 1995), Wu et al. (Proc. Nat'l. Acad. Sci. USA 92:11671-11675, 1995) and Thomson et al (J. Virol. 72:2246-2252, 1998) describe endosomal targeting signals (including invariant chain Ii and lysosomal-associated membrane protein LAMP-1) and their use in directing antigens to endosomal and/or lysosomal cellular compartments.

Endosomal targeting signals such as invariant chain also can be conjugated to SSX-4 protein or peptides by non-peptide bonds (i.e. not fusion proteins) to prepare a conjugate capable of specifically targeting SSX-4. Specific examples of covalent bonds include those wherein bifunctional cross-linker molecules are used. The cross-linker molecules may be homobifunctional or heterobifunctional, depending upon the nature of the molecules to be conjugated. Homobifunctional cross-linkers have two identical reactive groups. Heterobifunctional cross-linkers are defined as having two different reactive groups that allow for sequential conjugation reaction. Various types of commercially available cross-linkers are reactive with one or more of the following groups; primary amines, secondary amines, sulfhydryls, carboxyls, carbonyls and carbohydrates. One of ordinary skill in the art will be able to ascertain without undue experimentation the preferred molecule for linking the endosomal targeting moiety and SSX-4 peptide or protein, based on the chemical properties of the molecules being linked and the preferred characteristics of the bond or bonds.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a SSX-4 HLA class II binding peptide. That heterologous DNA (RNA) is placed under operable control of transcriptional elements to permit the expression of the heterologous DNA in the host cell. As described herein, such expression constructs optionally also contain nucleotide sequences which encode endosomal targeting signals, preferably human invariant chain or a targeting fragment thereof.

Preferred systems for mRNA expression in mammalian cells are those such as pRc/CMV and pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor la, which stimulates efficiently transcription in vitro. The plasmid is described by Mizushima and Nagata (*Nuc. Acids Res.* 18:5322, 1990), and its use in transfection experiments is disclosed by, for example, Demoulin (*Mol. Cell. Biol.* 16:4710-4716, 1996). Still another preferred expression vector is an adenovirus, described by Stratford-Perricaudet, which is defective for E1 and E3 proteins (*J. Clin. Invest.* 90:626-630, 1992). The use of the adenovirus as an Adeno.P1A recombinant is disclosed by Warnier et al., in intradermal injection in mice for immunization against P1A (*Int. J. Cancer,* 67:303-310, 1996). Recombinant vectors including viruses selected from the group consisting of adenoviruses, adeno-associated viruses, poxviruses including vaccinia viruses and attenuated poxviruses such as ALVAC, NYVAC, Semliki Forest virus, Venezuelan equine encephalitis virus, retroviruses, Sindbis virus, Ty virus-like particle, other alphaviruses, VSV, plasmids (e.g. "naked" DNA), bacteria (e.g. the bacterium Bacille Calmette Guerin, attenuated *Salmonella*), and the like can be used in such delivery, for example, for use as a vaccine.

The invention also embraces so-called expression kits, which allow the artisan to prepare a desired expression vector or vectors. Such expression kits include at least separate portions of at least two of the previously discussed materials. Other components may be added, as desired.

The invention as described herein has a number of uses, some of which are described herein. The following uses are described for SSX-4 HLA class II binding peptides but are equally applicable to use of other SSX family HLA class II binding peptides that are described herein. First, the invention permits the artisan to diagnose a disorder characterized by expression of a SSX-4 HLA class II binding peptide. These methods involve determining expression or presence in a biological sample of a SSX-4 HLA class II binding peptide, or a complex of a SSX-4 HLA class II binding peptide and an HLA class II molecule. The expression of a peptide or complex of peptide and HLA class II molecule can be determined by assaying with a binding partner for the peptide or complex, such as an antibody, a T lymphocyte, a multimeric complex of T cell receptors specific for the complex, and the like. Assays that are well known in the immunological arts can be employed, such as ELISA, ELISPOT, flow cytometry, and the like.

The invention further includes nucleic acid or protein microarrays with components that bind SSX-4 HLA class II peptides or nucleic acids encoding such polypeptides. In this aspect of the invention, standard techniques of microarray technology are utilized to assess expression of the SSX-4 polypeptides and/or identify biological constituents that bind such polypeptides. The constituents of biological samples include antibodies, lymphocytes (particularly T lymphocytes), T cell receptor molecules and the like. Protein microarray technology, which is also known by other names including: protein chip technology and solid-phase protein array technology, is well known to those of ordinary skill in the art and is based on, but not limited to, obtaining an array of identified peptides or proteins on a fixed substrate, binding target molecules or biological constituents to the peptides, and evaluating such binding. See, e.g., G. MacBeath and S. L. Schreiber, "Printing Proteins as Microarrays for High-Throughput Function Determination," *Science* 289(5485): 1760-1763, 2000. Nucleic acid arrays, particularly arrays that bind SSX-4 peptides also can be used for diagnostic applications, such as for identifying subjects that have a condition characterized by SSX-4 polypeptide expression.

Microarray substrates include but are not limited to glass, silica, aluminosilicates, borosilicates, metal oxides such as alumina and nickel oxide, various clays, nitrocellulose, or nylon. The microarray substrates may be coated with a compound to enhance synthesis of a probe (peptide or nucleic acid) on the substrate. Coupling agents or groups on the substrate can be used to covalently link the first nucleotide or amino acid to the substrate. A variety of coupling agents or groups are known to those of skill in the art. Peptide or nucleic acid probes thus can be synthesized directly on the substrate in a predetermined grid. Alternatively, peptide or nucleic acid probes can be spotted on the substrate, and in such cases the substrate may be coated with a compound to enhance binding of the probe to the substrate. In these embodiments, presynthesized probes are applied to the substrate in a precise, predetermined volume and grid pattern, preferably utilizing a computer-controlled robot to apply probe to the substrate in a contact-printing manner or in a non-contact manner such as ink jet or piezo-electric delivery. Probes may be covalently linked to the substrate.

Targets are peptides or proteins and may be natural or synthetic. The tissue may be obtained from a subject or may be grown in culture (e.g. from a cell line).

In some embodiments of the invention one or more control peptide or protein molecules are attached to the substrate. Preferably, control peptide or protein molecules allow determination of factors such as peptide or protein quality and binding characteristics, reagent quality and effectiveness, binding success, and analysis thresholds and success.

Nucleic acid microarray technology, which is also known by other names including: DNA chip technology, gene chip technology, and solid-phase nucleic acid array technology, is well known to those of ordinary skill in the art and is based on, but not limited to, obtaining an array of identified nucleic acid probes on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast*, Nature Genetics, Vol. 21, January 1999, the entire contents of which is incorporated by reference herein.

According to the present invention, nucleic acid microarray substrates may include but are not limited to glass, silica, aluminosilicates, borosilicates, metal oxides such as alumina and nickel oxide, various clays, nitrocellulose, or nylon. In all embodiments a glass substrate is preferred. According to the invention, probes are selected from the group of nucleic acids including, but not limited to: DNA, genomic DNA, cDNA, and oligonucleotides; and may be natural or synthetic. Oligonucleotide probes preferably are 20 to 25-mer oligonucleotides and DNA/cDNA probes preferably are 500 to 5000 bases in length, although other lengths may be used. Appropriate probe length may be determined by one of ordinary skill in the art by following art-known procedures. In one embodiment, preferred probes are sets of two or more molecule that bind the nucleic acid molecules that encode the SSX-4 HLA class II binding peptides set forth herein. Probes may be purified to remove contaminants using standard methods known to those of ordinary skill in the art such as gel filtration or precipitation.

In one embodiment, the microarray substrate may be coated with a compound to enhance synthesis of the probe on the substrate. Such compounds include, but are not limited to, oligoethylene glycols. In another embodiment, coupling agents or groups on the substrate can be used to covalently link the first nucleotide or olignucleotide to the substrate. These agents or groups may include, for example, amino, hydroxy, bromo, and carboxy groups. These reactive groups are preferably attached to the substrate through a hydrocarbyl radical such as an alkylene or phenylene divalent radical, one valence position occupied by the chain bonding and the remaining attached to the reactive groups. These hydrocarbyl groups may contain up to about ten carbon atoms, preferably up to about six carbon atoms. Alkylene radicals are usually preferred containing two to four carbon atoms in the principal chain. These and additional details of the process are disclosed, for example, in U.S. Pat. No. 4,458,066, which is incorporated by reference in its entirety.

In one embodiment, probes are synthesized directly on the substrate in a predetermined grid pattern using methods such as light-directed chemical synthesis, photochemical deprotection, or delivery of nucleotide precursors to the substrate and subsequent probe production.

In another embodiment, the substrate may be coated with a compound to enhance binding of the probe to the substrate. Such compounds include, but are not limited to: polylysine, amino silanes, amino-reactive silanes (Chipping Forecast, 1999) or chromium. In this embodiment, presynthesized probes are applied to the substrate in a precise, predetermined volume and grid pattern, utilizing a computer-controlled robot to apply probe to the substrate in a contact-printing manner or in a non-contact manner such as ink jet or piezo-electric delivery. Probes may be covalently linked to the substrate with methods that include, but are not limited to, UV-irradiation. In another embodiment probes are linked to the substrate with heat.

Targets for microarrays are nucleic acids selected from the group, including but not limited to: DNA, genomic DNA, cDNA, RNA, mRNA and may be natural or synthetic. In all embodiments, nucleic acid target molecules from human tissue are preferred. The tissue may be obtained from a subject or may be grown in culture (e.g. from a cell line).

In embodiments of the invention one or more control nucleic acid molecules are attached to the substrate. Preferably, control nucleic acid molecules allow determination of factors such as nucleic acid quality and binding characteristics, reagent quality and effectiveness, hybridization success, and analysis thresholds and success. Control nucleic acids may include but are not limited to expression products of genes such as housekeeping genes or fragments thereof.

The invention also permits the artisan to treat a subject having a disorder characterized by expression of a SSX-4 HLA class II binding peptide. Treatments include administering an agent which enriches in the subject a complex of a SSX-4 HLA class II binding peptide and an HLA class II molecule, and administering CD4$^+$ T lymphocytes which are specific for such complexes. Agents useful in the foregoing treatments include SSX-4 HLA class II binding peptides and functional variants thereof, proteins including such SSX-4 HLA class II binding peptides, optionally containing endosome targeting sequences fused to the SSX-4 sequences, nucleic acids which express such proteins and peptides (including viruses and other vectors that contain the nucleic acids), complexes of such peptides and HLA class II binding molecules (e.g., HLA-DR), antigen presenting cells bearing complexes of a SSX-4 HLA class II binding peptide and an HLA class II binding molecule (such as dendritic cells bearing one or more SSX-4 HLA class II binding peptides bound to HLA class II molecules), and the like. The invention also permits an artisan to selectively enrich a population of T lymphocytes for CD4+ T lymphocytes specific for a SSX-4 HLA class II binding peptide. Similar methods can be practiced using the SSX family peptides described herein as being structurally related to the SSX-4 HLA class II binding peptides.

The isolation of the SSX-4 HLA class II binding peptides also makes it possible to isolate and/or synthesize nucleic acids that encode the SSX-4 HLA class II binding peptides. Nucleic acids can be used to produce in vitro or in prokaryotic or eukaryotic host cells the SSX-4 HLA class II binding peptides.

Peptides comprising the SSX-4 HLA class II binding peptide of the invention may be synthesized in vitro, using standard methods of peptide synthesis, preferably automated peptide synthesis. In addition, a variety of other methodologies well-known to the skilled practitioner can be utilized to obtain isolated SSX-4 HLA class II binding peptides. For example, an expression vector may be introduced into cells to cause production of the peptides. In another method, mRNA transcripts may be microinjected or otherwise introduced into cells to cause production of the encoded peptides. Translation of mRNA in cell-free extracts such as the reticulocyte lysate system also may be used to produce peptides. Those skilled in the art also can readily follow known methods for isolating peptides in order to obtain isolated SSX-4 HLA class II binding peptides. These include, but are not limited to, immunochromatography, HPLC, size-exclusion chromatography, ion-exchange chromatography and immune-affinity chromatography.

These isolated SSX-4 HLA class II binding peptides, proteins which include such peptides, or complexes of the peptides and HLA class II molecules, such as HLA-DR, may be combined with materials such as adjuvants to produce vaccines useful in treating disorders characterized by expression of the SSX-4 HLA class II binding peptide. Preferably, vaccines are prepared from antigen presenting cells that present the SSX-4 HLA class II binding peptide/HLA class II complexes on their surface, such as dendritic cells, B cells, non-proliferative transfectants, etcetera. In all cases where cells are used as a vaccine, these can be cells transfected with coding sequences for one or both of the components necessary to stimulate CD4+ lymphocytes, or can be cells which already express both molecules without the need for transfection. For example, autologous antigen presenting cells can be isolated from a patient and treated to obtain cells which present SSX-4 epitopes in association of HLA class I and HLA class II molecules. These cells would be capable of stimulating both CD4+ and CD8+ cell responses. Such antigen presenting cells can be obtained by infecting dendritic cells with recombinant viruses encoding an Ii.SSX-4 fusion protein. Dendritic cells also can be loaded with HLA class I and HLA class II peptide epitopes.

Vaccines also encompass naked DNA or RNA, encoding a SSX-4 HLA class II binding peptide or precursor thereof, which may be produced in vitro and administered via injection, particle bombardment, nasal aspiration and other methods. Vaccines of the "naked nucleic acid" type have been demonstrated to provoke an immunological response including generation of CTLs specific for the peptide encoded by the naked nucleic acid (*Science* 259:1745-1749, 1993). Vaccines also include nucleic acids packaged in a virus, liposome or other particle, including polymeric particles useful in drug delivery.

The immune response generated or enhanced by any of the treatments described herein can be monitored by various methods known in the art. For example, the presence of T cells specific for a SSX-4 antigen can be detected by direct labeling of T cell receptors with soluble fluorogenic MHC molecule tetramers (or multimers) which present the antigenic SSX-4 peptide (Altman et al., *Science* 274:94-96, 1996; Dunbar et al., *Curr. Biol.* 8:413-416, 1998). Briefly, soluble MHC class 1 molecules are folded in vitro in the presence of β2-microglobulin and a peptide antigen which binds the class I molecule. After purification, the MHC/peptide complex is purified and labeled with biotin. Tetramers are formed by mixing the biotinylated peptide-MHC complex with labeled avidin (e.g. phycoerythrin) at a molar ratio of 4:1. Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein. The use of MHC class II molecules as tetramers was recently demonstrated by Crawford et al. (*Immunity* 8:675-682, 1998; see also Dunbar and Ogg, *J. Immunol. Methods* 268(1):3-7, 2002; Arnold et al., *J. Immunol. Methods* 271(1-2):137-151, 2002). Multimeric soluble MHC class II molecules were complexed with a covalently attached peptide (which can be attached with or without a linker molecule), but peptides also can be loaded onto class II molecules. The class II tetramers were shown to bind with appropriate specificity and affinity to specific T cells. Thus tetramers can be used to monitor both CD4+ and CD8+ cell responses to vaccination protocols. Methods for preparation of multimeric complexes of MHC class II molecules are described in Hugues et al., *J. Immunological Meth.* 268: 83-92 (2002) and references cited therein, each of which is incorporated by reference.

The SSX-4 HLA class II binding peptide, as well as complexes of SSX-4 HLA class II binding peptide and HLA molecule, also may be used to produce antibodies, using standard techniques well known to the art. Standard reference works setting forth the general principles of antibody production include Catty, D., *Antibodies, A Practical Approach*, Vol. 1, IRL Press, Washington D.C. (1988); Klein, J., *Immunology: The Science of Cell-Non-Cell Discrimination*, John Wiley and Sons, New York (1982); Kennett, R., et al., *Monoclonal Antibodies, Hybridoma, A New Dimension In Biological Analyses*, Plenum Press, New York (1980); Campbell, A., *Monoclonal Antibody Technology*, in *Laboratory Techniques and Biochemistry and Molecular Biology*, Vol. 13 (Burdon, R. et al. EDS.), Elsevier Amsterdam (1984); and Eisen, H. N., *Microbiology*, third edition, Davis, B. D. et al. EDS. (Harper & Rowe, Philadelphia (1980).

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody.

Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816, 567, 5,225,539, 5,585,089, 5,693,762 and 5,859,205.

Fully human monoclonal antibodies also can be prepared by immunizing mice transgenic for large portions of human immunoglobulin heavy and light chain loci. See, e.g., U.S. Pat. Nos. 5,545,806, 6,150,584, and references cited therein. Following immunization of these mice (e.g., XENOMOUSE (Abgenix), HUMAB-MOUSE (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The antibodies of the present invention thus are prepared by any of a variety of methods, including administering protein, fragments of protein, cells expressing the protein or fragments thereof and an appropriate HLA class II molecule, and the like to an animal to induce polyclonal antibodies. The production of monoclonal antibodies is according to techniques well known in the art. Antibodies prepared according to the invention also preferably are specific for the peptide/HLA complexes described herein.

The antibodies of this invention can be used for experimental purposes (e.g., localization of the HLA/peptide complexes, immunoprecipitations, Western blots, flow cytometry, ELISA etc.) as well as diagnostic or therapeutic purposes (e.g., assaying extracts of tissue biopsies for the presence of the SSX-4 peptides, HLA/peptide complexes, targeting delivery of cytotoxic or cytostatic substances to cells expressing the appropriate HLA/peptide complex). The antibodies of this invention are useful for the study and analysis of antigen presentation on tumor cells and can be used to assay for changes in the HLA/peptide complex expression before, during or after a treatment protocol, e.g., vaccination with peptides, antigen presenting cells, HLA/peptide tetramers, adoptive transfer or chemotherapy.

The antibodies and antibody fragments of this invention may be coupled to diagnostic labeling agents for imaging of cells and tissues that express the HLA/peptide complexes or may be coupled to therapeutically useful agents by using standard methods well-known in the art. The antibodies also may be coupled to labeling agents for imaging e.g., radiolabels or fluorescent labels, or may be coupled to, e.g., biotin or antitumor agents, e.g., radioiodinated compounds, toxins such as ricin, methotrexate, cytostatic or cytolytic drugs, etc. Examples of diagnostic agents suitable for conjugating to the antibodies of this invention include e.g., barium sulfate, diatrizoate sodium, diatrizoate meglumine, iocetamic acid, iopanoic acid, ipodate calcium, metrizamide, tyropanoate sodium and radiodiagnostics including positron emitters such as fluorine-18 and carbon-11, gamma emitters such as iodine-123, technitium-99 m, iodine-131 and indium-111, nuclides for nuclear magnetic resonance such as fluorine and gadolinium. As used herein, "therapeutically useful agents" include any therapeutic molecules, which are preferably targeted selectively to a cell expressing the HLA/peptide complexes, including antineoplastic agents, radioiodinated compounds, toxins, other cytostatic or cytolytic drugs. Antineoplastic therapeutics are well known and include: aminoglutethimide, azathioprine, bleomycin sulfate, busulfan, carmustine, chlorambucil, cisplatin, cyclophosphamide, cyclosporine, cytarabidine, dacarbazine, dactinomycin, daunorubicin, doxorubicin, taxol, etoposide, fluorouracil, interferon-.alpha., lomustine, mercaptopurine, methotrexate, mitotane, procarbazine HCl, thioguanine, vinblastine sulfate and vincristine sulfate. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division). Toxins can be proteins such as, for example, pokeweed anti-viral protein, cholera toxin, pertussis toxin, ricin, gelonin, abrin, diphtheria exotoxin, or *Pseudomonas* exotoxin. Toxin moieties can also be high energy-emitting radionuclides such as cobalt-60. The antibodies may be administered to a subject having a pathological condition characterized by the presentation of the HLA/peptide complexes of this invention, e.g., melanoma or other cancers, in an amount sufficient to alleviate the symptoms associated with the pathological condition.

When "disorder" or "condition" is used herein, it refers to any pathological condition where the SSX-4 protein or HLA class II binding peptide is expressed. Such disorders include cancers, such as biliary tract cancer; bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemias, multiple myeloma, AIDS-associated leukemias and adult T-cell leukemia lymphoma; intraepithelial neoplasms including Bowen's disease and Paget's disease; liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilms tumor.

Some therapeutic approaches based upon the disclosure are premised on inducing a response by a subject's immune system to SSX HLA class II binding peptide presenting cells. One such approach is the administration of autologous CD4$^+$ T cells specific to the complex of SSX-4 HLA class II binding peptide and an HLA class II molecule to a subject with abnormal cells of the phenotype at issue. It is within the skill of the artisan to develop such CD4$^+$ T cells in vitro. Generally, a sample of cells taken from a subject, such as blood cells, are contacted with a cell presenting the complex and capable of provoking CD4$^+$ T lymphocytes to proliferate. The target cell can be a transfectant, such as a COS cell, or an antigen presenting cell bearing HLA class II molecules, such as dendritic cells or B cells preferably autologous APCs such as dendritic cells (DC) purified from PBMC. DC could be transfected of pulsed with antigen, either full length protein or peptide. (Ayyoub, M et al J. Immunol. 2004 172:7206-7211, Ayyoub M. et al. J Clin Invest 2004 113:1225-33.) These transfectants present the desired complex of their surface and, when combined with a CD4$^+$ T lymphocyte of interest, stimulate its proliferation. COS cells are widely available, as are other suitable host cells. Specific production of CD4$^+$ T lymphocytes is described below. The clonally expanded autologous CD4$^+$ T lymphocytes then are administered to the subject. The CD4$^+$ T lymphocytes then stimulate the subject's immune response, thereby achieving the desired therapeutic goal.

CTL proliferation can be increased by increasing the level of tryptophan in T cell cultures, by inhibiting enzymes which catabolizes tryptophan, such as indoleamine 2,3-dioxygenase (IDO), or by adding tryptophan to the culture (see, e.g., PCT application WO99/29310). Proliferation of T cells is enhanced by increasing the rate of proliferation and/or extending the number of divisions of the T cells in culture. In addition, increasing tryptophan in T cell cultures also enhances the lytic activity of the T cells grown in culture.

The foregoing therapy assumes that at least some of the subject's abnormal cells present the relevant HLA/peptide complex. This can be determined very easily, as the art is very familiar with methods for identifying cells which present a particular HLA molecule, as well as how to identify cells expressing DNA of the pertinent sequences, in this case a SSX-4 sequence.

The foregoing therapy is not the only form of therapy that is available in accordance with the invention. CD4$^+$ T lymphocytes can also be provoked in vivo, using a number of approaches. One approach is the use of non-proliferative cells expressing the complex. The cells used in this approach may be those that normally express the complex, such as dendritic cells or cells transfected with one or both of the genes necessary for presentation of the complex. Chen et al., (*Proc. Natl. Acad. Sci. USA* 88: 110-114, 1991) exemplifies this approach, showing the use of transfected cells expressing HPV-E7 peptides in a therapeutic regime. Various cell types may be used. Similarly, vectors carrying one or both of the genes of interest may be used. Viral or bacterial vectors are especially preferred. For example, nucleic acids which encode a SSX-4 HLA class II binding peptide may be operably linked to promoter and enhancer sequences which direct expression of the SSX-4 HLA class II binding peptide in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding SSX-4 HLA class II binding peptides. Nucleic acids encoding a SSX-4 HLA class II binding peptide also may be inserted into a retroviral genome, thereby facilitating integration of the nucleic acid into the genome of the target tissue or cell type. In these systems, the gene of interest is carried by a microorganism, e.g., a Vaccinia virus, poxviruses in general, adenovirus, herpes simplex virus, retrovirus or the bacteria BCG, and the materials de facto "infect" host cells. The cells which result present the complex of interest, and are recognized by autologous CD4$^+$ T cells, which then proliferate.

A similar effect can be achieved by combining a SSX HLA class II binding peptide with an adjuvant to facilitate incorporation into HLA class II presenting cells in vivo. If larger than the HLA class II binding portion (e.g., SEQ ID NOs:5, 6, 7, 8, 9 and 10), the SSX-4 HLA class II binding peptide can be processed if necessary to yield the peptide partner of the HLA molecule while the peptides disclosed herein are believed to be presented without the need for further processing. Generally, subjects can receive an intradermal, intravenous, subcutaneous or intramuscular injection of an effective amount of the SSX-4 HLA class II binding peptide. Initial doses can be followed by bi- or tri-weekly, weekly or monthly booster doses, following immunization protocols standard in the art.

A preferred method for facilitating incorporation of SSX-4 HLA class II binding peptides into HLA class II presenting cells is by expressing in the presenting cells a polypeptide which includes an endosomal targeting signal fused to a SSX-4 polypeptide which includes the class II binding peptide. Particularly preferred are SSX-4 fusion proteins which contain human invariant chain Ii.

Any of the foregoing compositions or protocols can include also SSX HLA class I binding peptides for induction of a cytolytic T lymphocyte response. For example, the SSX-4 protein can be processed in a cell to produce both HLA class I and HLA class II responses. SSX gene and protein family members are disclosed in U.S. Pat. Nos. 6,291,658 and 6,339,140. By administering SSX-4 peptides which bind HLA class I and class II molecules (or nucleic acid encoding such peptides), an improved immune response may be provided by inducing both T helper cells and cytotoxic T cells.

In addition, non-SSX-4 tumor associated peptides also can be administered to increase immune response via HLA class I and/or class II. It is well established that cancer cells can express more that one tumor associated gene. It is within the scope of routine experimentation for one of ordinary skill in the art to determine whether a particular subject expresses additional tumor associated genes, and then include HLA class I and/or HLA class II binding peptides derived from expression products of such genes in the foregoing SSX-4 compositions and vaccines.

Especially preferred are nucleic acids encoding a series of epitopes, known as "polytopes". The epitopes can be arranged in sequential or overlapping fashion (see, e.g., Thomson et al., *Proc. Natl. Acad. Sci. USA* 92:5845-5849, 1995; Gilbert et al., *Nature Biotechnol.* 15:1280-1284, 1997), with or without the natural flanking sequences, and can be separated by unrelated linker sequences if desired. The polytope is processed to generated individual epitopes which are recognized by the immune system for generation of immune responses.

Thus, for example, SSX-4 HLA class II binding peptides can be combined with peptides from other tumor rejection antigens (e.g. by preparation of hybrid nucleic acids or polypeptides) and with SSX-4 HLA class I binding peptides (some of which are listed below) to form "polytopes". Exemplary tumor associated peptide antigens that can be administered to induce or enhance an immune response are derived from tumor associated genes and encoded proteins including MAGE-A1, MAGE-A2, MAGE-A3, MAGE-A4, MAGE-A5, MAGE-A6, MAGE-A7, MAGE-A8. MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), tyrosinase, brain glycogen phosphorylase, Melan-A, MAGE-C1 (CT-7), MAGE-C2, NY-ESO-1, LAGE-1, SSX-1, SSX-2, SSX-3, SSX-5, SCP-1 and CT-10. For example, antigenic peptides characteristic of tumors include those listed in published PCT application WO 00/20581 (PCT/US99/21230).

Other examples of HLA class I and HLA class II binding peptides will be known to one of ordinary skill in the art (for example, see Coulie, *Stem Cells* 13:393-403, 1995), and can be used in the invention in a like manner as those disclosed herein. One of ordinary skill in the art can prepare polypeptides comprising one or more SSX-4 peptides and one or more of the foregoing tumor rejection peptides, or nucleic acids encoding such polypeptides, according to standard procedures of molecular biology.

Thus polytopes are groups of two or more potentially immunogenic or immune response stimulating peptides which can be joined together in various arrangements (e.g. concatenated, overlapping). The polytope (or nucleic acid encoding the polytope) can be administered in a standard immunization protocol, e.g. to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., *Proc. Acad. Natl. Acad. Sci. USA* 92(13):5845-5849, 1995; Gilbert et al., *Nature Biotechnol.* 15(12):1280-1284, 1997; Thomson et al., *J. Immunol.* 157(2):822-826, 1996; Tam et al., *J. Exp. Med.* 171(1):299-306, 1990). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognized by CTLs. Thus polytopes containing various numbers and combinations of epitopes can be prepared and tested for recognition by CTLs and for efficacy in increasing an immune response.

It is known that tumors express a set of tumor antigens, of which only certain subsets may be expressed in the tumor of any given patient. Polytopes can be prepared which correspond to the different combination of epitopes representing the subset of tumor rejection antigens expressed in a particular patient. Polytopes also can be prepared to reflect a broader spectrum of tumor rejection antigens known to be expressed by a tumor type. Polytopes can be introduced to a patient in need of such treatment as polypeptide structures, or via the use of nucleic acid delivery systems known in the art (see, e.g., Allsopp et al., *Eur. J. Immunol.* 26(8):1951-1959, 1996). Adenovirus, pox virus, Ty-virus like particles, adeno-associated virus, plasmids, bacteria, etc. can be used in such delivery. One can test the polytope delivery systems in mouse models to determine efficacy of the delivery system. The systems also can be tested in human clinical trials.

As part of the immunization compositions, one or more substances that potentiate an immune response are administered along with the peptides described herein. Such substances include adjuvants and cytokines. An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of *Salmonella minnesota* Re 595 lipopolysaccharide; saponins including QS21 (SmithKline Beecham), a pure QA-21 saponin purified from *Quillja saponaria* extract; DQS21, described in PCT application WO96/33739 (SmithKline Beecham); ISCOM (CSL Ltd., Parkville, Victoria, Australia) derived from the bark of the *Quillaia saponaria* molina tree; QS-7, QS-17, QS-18, and QS-L1 (So et al., *Mol. Cells.* 7:178-186, 1997); incomplete Freund's adjuvant; complete Freund's adjuvant; montanide; immunostimulatory oligonucleotides (see e.g. CpG oligonucleotides described by Krieg et al., *Nature* 374:546-9, 1995); reagents that bind to one of the toll-like receptors; vitamin E and various water-in-oil emulsions prepared from biodegradable oils such as squalene and/or tocopherol; and factors that are taken up by the so-called 'toll-like receptor 7' on certain immune cells that are found in the outside part of the skin, such as imiquimod (3M, St. Paul, Minn.). Preferably, the peptides are administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 µg to about 100 µg. Other adjuvants are known in the art and can be used in the invention (see, e.g. Goding, *Monoclonal Antibodies: Principles and Practice,* 2nd Ed., 1986). Methods for the preparation of mixtures or emulsions of peptide and adjuvant are well known to those of skill in the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., *Science* 268: 1432-1434, 1995), GM-CSF, IL-18 and IL-15 (Klebanoff et al. Proc. Natl. Acad. Sci. USA 2004 101:1969-74). Thus cytokines can be administered in conjunction with antigens and adjuvants to increase the immune response to the antigens. There are a number of additional immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation, and effector function. B7 also interacts with CTLA4 (CD152) on T cells and studies involving CTLA4 and B7 ligands indicate that the B7-CTLA4 interaction can enhance antitumor immunity and CTL proliferation (Zheng et al., *Proc. Nat'l Acad. Sci. USA* 95:6284-6289, 1998).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., *J. Immunol.* 154:5637-5648, 1995). Tumor cell transfection with B7 has been discussed in relation to in vitro CTL expansion for adoptive transfer immunotherapy by Wang et al. (*J. Immunother Emphasis Tumor Immunol* 19:1-8, 1996). Other delivery mechanisms for the B7 molecule would include nucleic acid (naked DNA) immunization (Kim et al., *Nature Biotechnol.* 15:7:641-646, 1997) and recombinant viruses such as adeno and pox (Wendtner et al., *Gene Ther.* 4:726-735, 1997). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered. Similarly, the inducible co-stimulatory molecule ICOS which induces T cell responses to foreign antigen could be modulated, for example, by use of anti-ICOS antibodies (Hutloff et al., *Nature* 397:263-266, 1999).

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J. Immunol.*, 158:637-642, 1997; Fenton et al., *J. Immunother.*, 21:95-108, 1998).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., 1998). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., *Nature* 393:474, 1998; Bennett et al., *Nature* 393:478, 1998; Schoenberger et al., *Nature* 393:480, 1998). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumor associated antigens which are normally encountered outside of an inflammatory context or are presented by non-professional APCs (tumor cells). Other methods for inducing maturation of dendritic cells, e.g., by increasing CD40-CD40L interaction, or by contacting DCs with CpG-containing oligodeoxynucleotides or stimulatory sugar moieties from extracellular matrix, are known in the art. In these situations Th help and B7 costimulation signals are not provided. This mechanism might be used in the context of antigen pulsed DC based therapies or in situations where Th epitopes have not been defined within known tumor associated antigen precursors.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. In the case of inducing an immune response, the desired response is an increase in antibodies or T lymphocytes which are specific for the SSX-4 immunogen(s) employed. These desired responses can be monitored by routine methods or can be monitored according to diagnostic methods of the invention discussed herein.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 milligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

EXAMPLES

Materials and methods
Cells and Tissue Culture.

Peripheral blood was obtained from healthy donors (NYC Blood Bank) and melanoma patients (Lausanne University Hospital, Switzerland) upon informed consent. Melanoma cell lines, anti HLA-DR (D1.12), and -DP (B7.21.3) antibodies were provided by Dr. D. Rimoldi (LICR, Lausanne, Switzerland). Cell lines were maintained in RPMI 1640 (GIBCO, Rockville, Md., USA) supplemented with 10% heat inactivated fetal calf serum (FCS). Culture medium for lymphocytes was IMDM (GIBCO) supplemented with 8% heat inactivated pooled human serum (CTL medium), recombinant human (rh) IL-2 (Glaxo, Geneva, Switzerland) and rh IL-7 (R&D, Minneapolis, Minn., USA). Homozygous EBV transformed B cell lines (EBV-B) were obtained from the National Marrow Donor Program/American Society for Histocompatibility and Immunogenetics (NMDP/ASHI) Cell Repository.
Generation of SSX-4 Specific CD4+ T Cells.

In vitro stimulation of SSX-4 specific T cells was carried out as described previously (Ayyoub, M., et al., 2004, An immunodominant SSX-2-derived epitope recognized by CD4+ T cells in association with HLA-DR, *J Clin Invest*, 113:1225-1233). Briefly, 1 to $2 \times 10^6$ CD4+ T cells highly enriched (>90%) from PBMC by magnetic cell sorting using a miniMACS magnetic cell separator device (Miltenyi Biotec, Auburn, Calif., USA) were stimulated with autologous antigen presenting cells in the presence of a pool of partially overlapping peptides spanning the entire SSX-4 protein sequence (2 μM each). Two weeks later the culture was tested using the same peptide pool or individual peptides from the pool, as indicated. CD4+ T cells secreting IFN-γ in response to peptide stimulation were isolated by cytokine guided magnetic cell sorting using the cytokine secretion detection kit (Miltenyi Biotec) and cloned by limiting dilution culture in the presence of PHA (Sigma, St Louis, Mo., USA), allogeneic irradiated PBMC and rhIL-2 as described (Ayyoub, M., et al., 2004, *J Clin Invest*, 113:1225-1233). Clones were subsequently expanded by periodic (3-4 weeks) stimulation under the same conditions.

Antigen Recognition Assays.

For intracellular cytokine secretion detection, T cells were stimulated in the absence or in the presence of peptides at the indicated dose during 4 h as described previously (Ayyoub, M., et al., 2004, *J Clin Invest*, 113:1225-1233). One hour after the beginning of the incubation, Brefeldin A (10 μg/ml, Sigma) was added to inhibit cytokine secretion. After incubation, cells were stained with anti-CD4 mAb (Becton Dickinson, San Diego, Calif., USA) for 20 min at 4° C. and fixed using formaldehyde, permeabilized with saponine (Sigma, 0.1% in PBS 5% FCS), stained with anti IFN-γ mAb (BD Pharmingen, San Diego, Calif., USA) and analyzed by flow cytometry. Data analysis was performed using Cell Quest software. IFN-γ secretion was assessed as described (Ayyoub, M., et al., 2004, *J Clin Invest*, 113:1225-1233). T cells (10,000) were incubated in the absence or in the presence of peptides at the indicated dose in 96-well round-bottom plates in 200 μl/well of medium. Where indicated, APC (EBV-B cells, 10,000/well) preincubated or not with antigen and extensively washed, were added. In some experiments tumor cells were used as APC. Where indicated, tumor cells were transiently transfected with SSX-4 cDNA, cloned into pcDNA3.1 vector, using FUGENE (reagent for transferring nucleic acid inside cells) according to the manufacturer's instructions (Roche Diagnostics, Indianapolis, Ind., USA). After 24 h incubation at 37° C., culture supernatants were collected and the content of IFN$_I$ determined by ELISA (BioSource International, Camarillo, Calif., USA).

Generation of DC and Recombinant Proteins.

Monocyte derived DC were prepared from CD 14+ monocytes isolated from PBMC by magnetic cell sorting using miniMACS (magnetic cell separator device, Miltenyi Biotec). Highly enriched CD14+ cells (purity >95%) were cultured in CTL medium containing 1,000 U/ml of rh GM-CSF and 1,000 U/ml of rh IL-4 (R&D) during 6 days. SSX-4 protein was expressed by cloning of full-length cDNA into pQE30 (Qiagen, Valencia, Calif., USA) and synthesized in *Escherichia coli* with a six-histidine tag at the amino terminus. The protein was purified by nickel chelate affinity chromatography (HIS-BIND Resin (synthetic resin for polypeptide purification), Novagen, La Jolla, Calif., USA) by using a pH gradient, and eluting in 8 M urea, 100 mM phosphate, and 10 mM Tris at pH 4.5, followed by step gradient dialysis to 2 mM urea in PBS. Where indicated, DC were incubated with proteins for 12 hours and washed prior to their use in antigen recognition assay.

Results

Assessment of SSX-4 Specific CD4+ T Cell Responses in Circulating Lymphocytes from Melanoma Patients.

We analyzed CD4+ T cell responses to SSX-4 in circulating lymphocytes from 4 melanoma patients with detectable SSX-4 expression in the autologous tumor sample and/or autologous tumor line. CD4+ T cells were isolated from patients' PBMC by magnetic cell sorting and stimulated in vitro with a pool containing 20 amino acid long peptides overlapping by 10 amino acids and spanning the SSX-4 protein sequence, in the presence of irradiated autologous antigen presenting cells (APC). As internal control, PBMC samples from 4 healthy donors were processed and stimulated under the same conditions. Cultures were tested using the SSX-4 peptide pool for the presence of specific, IFN$_I$ secreting CD4+ T cells, by staining with IFN-γ and CD4-specific monoclonal antibodies (FIG. 1A). After the first cycle of in vitro stimulation (Table 1) no clear responses were detectable in patients' samples, although the proportion of IFN-γ secreting CD4+ T cells was 2 to 3 fold higher in the presence than in the absence of the peptide pool in the case of 3/4 patients. In contrast, after the second cycle of in vitro stimulation, specific responses to the SSX-4 peptide pool were clearly detected for 3/4 patients. Namely, for LAU 14, LAU 331 and LAU 97, a 20, 7 and 120-fold increased frequency of IFN-γ secreting CD4+ T cells was detected in the presence than in the absence of SSX-4 peptide pool, respectively. In the case of the fourth patient (LAU 672), however, the frequency of IFN-γ secreting CD4+ T cells obtained in the presence of the SSX-4 peptides pool was only 3 fold higher as compared to background values. It is noteworthy that in the case of the healthy donors assessed under identical conditions we failed to detect any specific response (Table 1).

TABLE 1

Assessment of SSX-4 specific CD4+ T cell responses in circulating lymphocytes from melanoma patients and healthy donors

| Code | IVS-1 | | IVS-2 | | CD4+ IFN-γ+ after isolation | |
|---|---|---|---|---|---|---|
| | −P | +P | −P | +P | negative fraction | positive fraction |
| LAU 14 | 0.06[A] | 0.06 | 0.02 | 0.40 | 5.8 | 64.1 |
| LAU 672 | 0.11 | 0.27 | 0.01 | 0.03 | 0.5 | 75.9 |
| LAU 331 | 0.02 | 0.06 | 0.07 | 0.54 | 2.1 | 87.9 |
| LAU 97 | 0.02 | 0.05 | 0.02 | 2.47 | 1.6 | 81.9 |
| HD 38110 | —[B] | — | 0.01 | 0.02 | <0.01 | <0.01 |
| HD 63 | — | — | <0.01 | 0.01 | <0.01 | <0.01 |
| HD 8927 | — | — | <0.01 | 0.01 | <0.01 | <0.01 |
| HD 8929 | — | — | 0.01 | 0.01 | <0.01 | <0.01 |

CD4+ T cells from patients (LAU) and donors (HD) were stimulated once (IVS-1), or twice (IVS-2), with a pool of 20 amino acid long and partially overlapping peptides encompassing the complete sequence of the SSX-4 antigen. Cultures were then assessed functionally in the absence (−P) or in the presence (+P) of the same peptide pool.
[A]percent of CD4+ IFNγ secreting cells;
[B]not done Assessment of Active Peptides in the SSX-4 Peptide Pool.

For 3 of the 4 patients enough cells were available from the cultures that had undergone two cycles of in vitro stimulation to assess reactivity to individual SSX-4 peptides. The results of this analysis are shown in Table 2. For each patient, reactivity was detected towards more than one peptide, indicating recognition of multiple epitopes in the SSX-4 sequence. The active peptides, however, were mostly different for each patient. For patient LAU 14, we identified two active peptides (61-80 and 101-120) at distinct locations of the protein sequence. For patient LAU 331 two active overlapping peptides (51-70 and 61-80) were identified. In addition, reactivity was also detected towards a third peptide at a different location (31-50). We obtained similar results in the case of patient LAU 97. Namely, the main activity was detected for peptide 151-170 with a lower proportion of IFN-γ secreting CD4+ T cells detected upon stimulation with the partially overlapping peptide 161-180. In addition, a third peptide at a distinct location, 41-60, stimulated IFN-γ production by a lower proportion of CD4+ T cells. It is noteworthy that, in all cases, the proportion of IFN-γ secreting CD4+ T cells detected in the presence of the peptide mix containing all overlapping peptides was much lower than that of both the sum of individual activities and of that of the most active peptide in the mixture, when tested individually. For example 9.43% of the cells in the culture from patient LAU 97 produced IFN-γ upon stimulation with peptide SSX-4 151-170, whereas the proportion of IFN-γ secreting cells detected in the presence of the SSX-4 peptide pool was about 3 times lower (3.55%).

TABLE 2

Assessment of active peptides in the SSX-4 peptide pool

| SSX-4 | LAU 97 | LAU 331 | LAU 14 |
|---|---|---|---|
| No peptide | 0.02[4] | 0.03 | 0.03 |
| All peptides | 3.55 | 0.18 | 0.20 |
| 1-20 | <0.01 | <0.01 | 0.07 |
| 11-30 | <0.01 | 0.02 | <0.01 |
| 21-40 | <0.01 | 0.02 | 0.04 |
| 31-50 | <0.01 | 0.34 | 0.01 |
| 41-60 | 0.20 | 0.02 | <0.01 |
| 51-70 | <0.01 | 0.65 | 0.06 |
| 61-80 | 0.03 | 0.16 | 0.12 |
| 71-90 | <0.01 | 0.05 | 0.03 |
| 81-100 | 0.02 | 0.02 | <0.01 |
| 91-110 | <0.01 | 0.02 | 0.03 |
| 101-120 | <0.01 | 0.02 | 0.91 |
| 111-130 | <0.01 | 0.01 | 0.01 |
| 121-140 | <0.01 | 0.01 | <0.01 |
| 131-150 | <0.01 | 0.02 | 0.01 |
| 141-160 | <0.01 | 0.01 | 0.03 |
| 151-170 | 9.43 | 0.01 | 0.01 |
| 161-180 | 2.25 | <0.01 | <0.01 |
| 171-188 | 0.01 | 0.02 | <0.01 |

The activity of individual SSX-4 peptides was assessed after the second cycle of in vitro stimulation with the SSX-4 peptide pool.
[4]Numbers are percent of CD4+ IFN-γ secreting cells.
Values at least 3 fold higher than baseline (no peptide) were considered significant and are underlined.

Isolation of Clonal SSX-4 Specific CD4+ T Cells from Cultures Stimulated with the SSX-4 Peptide Pool and Assessment of MHC Class II Restriction.

Figure 2:
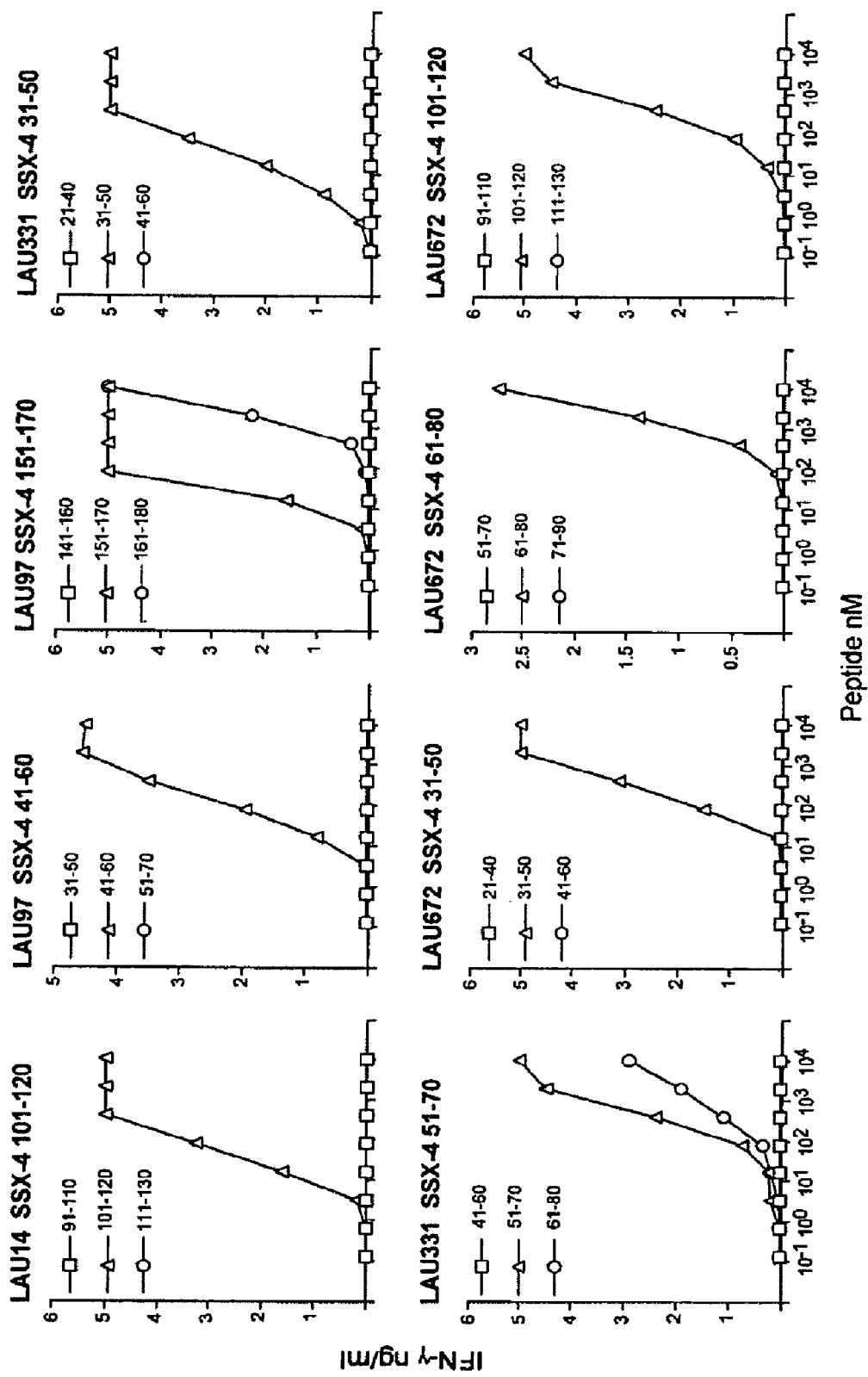
FIG. 2. Recognition of SSX-4 peptides by specific CD4+ T cell clones from melanoma patients. Antigen recognition by specific CD4+ T cell clones was assessed in the presence of graded peptide dilutions. For clones specific for each of the identified epitopes, antigen recognition was assessed for the corresponding active peptide as well as for neighboring overlapping peptides. The concentration of IFN-γ in the culture supernatant was assessed by ELISA after 24 h of culture as detailed in the methods section.

CD4+ T cells specifically secreting IFN-γ in response to stimulation with SSX-4 peptides were isolated from the cultures using a cytokine secretion detection kit (FIG. 1B). In the case of cultures from the melanoma patients, this method resulted in the isolation of highly enriched populations of CD4+ IFN-γ secreting T cells. In contrast, in the case of the cultures from the healthy donors, no CD4+ IFN-γ secreting T cells could be isolated following the same procedure (Table 1). Purified populations were cloned under limiting dilution conditions and the obtained clonal CD4+ T cell populations were used to further define and characterize the corresponding epitopes. Peptide titration curves for representative clones specific for each of the identified epitopes are shown in FIG. 2. In the majority of the cases the CD4+ T cell clones recognized the corresponding active peptide but not the neighboring overlapping peptides. In two cases, however, and in agreement with the findings reported in Table 2, recognition of one of the overlapping peptides was observed. This was the case for SSX-4 51-70 specific clones from LAU 331, that recognized peptide SSX-4 61-80, and for SSX-4 151-170 specific clones from LAU 97, that recognized peptide SSX-4 161-180 (FIG. 2).

To identify the MHC class II restricting element used by SSX-4 specific CD4+ T cell clones we initially performed peptide presentation experiments in the presence of antibodies known to specifically block antigen recognition restricted by different MHC class II molecules. An example of the data obtained with this analysis is shown in FIG. 3A and results obtained for all clones are summarized in Table 3. To establish the presenting allele(s) we first assessed by molecular typing the HLA-DR or HLA-DP alleles of the patients, depending on the restriction of the corresponding clones (Table 3). We then assessed presentation by homozygous EVB-B cells expressing each of the patient's alleles. An example of these experiments is shown in FIG. 3B and the results obtained for all clones are summarized in Tables 3 and 4.

The results obtained following this approach indicated the presence of two different epitopes corresponding to the activity of peptide SSX-4 31-50. In the case of 31-50 specific clones from patient LAU 331, the candidate restricting DRB1* allele was DRB1*0301. Presentation by the DRB3*0101 allele, which was expressed by the patient and by the homozygous EBV-B cell line COX, was excluded as no presentation was obtained using 0MV (DRB1*1301, DRB3*0101 homozygous). It is noteworthy that we have recently identified the homologous SSX-2 peptide (SSX-2 37-51) as a DRB1*0301 restricted epitope (submitted for publication). When assessed in a peptide titration assay, peptide SSX-4 37-51 was well recognized by SSX-4 31-50 reactive CD4+ T cells from LAU 331, although slightly less efficiently as compared to peptide SSX-4 31-50 (3 fold). Peptide SSX-2 37-51, however, was not recognized by SSX-4 specific CD4+ T cells (not shown). Interestingly, in the case of 31-50 specific clones from patient LAU 672, and despite the fact that this patient also expressed DRB1*0301, DRB1*0301 homozygous EBV-B cells pulsed with SSX-4 31-50 were unable to present the peptide to specific clones. In contrast, efficient presentation was obtained using two DRB1*1101 homozygous EBV-B cell lines (JBUSH and EBV-B from patient LAU 14). Presentation by the DRB3*0202 allele was excluded, as no presentation was obtained using 31227ABO (DRB1*1401, DRB3*0202 homozygous).

From patient LAU 672 we obtained SSX-4 specific CD4+ T cell clones recognizing two additional peptides 61-80 and 101-120, in association with HLA DR. For both, based on results obtained with HLA typed APC, DRB1*1101 was the restricting DR allele. In the case of SSX-4 101-120 specific CD4+ T cells from LAU 14, DRB1*1101 was also the restricting DR allele. Peptide SSX-4 41-60 was recognized by specific clones from patient LAU 97 in association with HLA-DR. Based on the results obtained with HLA typed APC, the restricting DRB1 allele was DRB1*1501(see Table 3). It is noteworthy that LAU 97 also expressed two additional DR alleles, DRB3*0101 and DRB5*0101. Presentation through DRB3*0101 could be excluded as this allele was also expressed by the EBV-B cell lines 0MW and COX that were unable to present the peptide to CD4+ T cells. Presentation through DRB5*0101, however, could not be formally excluded because of the lack of appropriate APC. In the case of peptide SSX-4 51-70, recognized by specific clones from patient LAU 331 in association with HLA-DR, based on the results obtained with HLA typed APC, the restricting DR allele was DRB1*0701 (see Table 3). Restriction by the two additional HLA-DR alleles expressed by the patient (DRB3*0101, DRB4*0101) could be excluded on the base of negative peptide presentation experiments with EBV-B cell lines expressing these alleles. Finally, peptide SSX-4 151-170 was recognized by CD4+ T cells from LAU 97 in association with HLA-DP. Based on peptide presentation experiments with HLA typed APC, the restricting DP allele was DPB1*1001.

TABLE 4

Identification of the restricting HLA class II allele(s) for SSX-4 specific CD4+ T cell clones

| Patient code | HLA class II molecular typing | Active peptide | Restricting MHC class II element | Restricting MHC class II allele |
|---|---|---|---|---|
| LAU 14 | DRB1*1101; DRB3*0202 | 101-120 | DR | DRB1*1101 |
| LAU 97 | DRB1*1301/1501; DRB3*0101, DRB5*0101 | 41-60 | DR | DRB1*1501 or DRB5*0101 |
| | DPB1*0402/1001 | 151-170 | DP | DPB1*1001 |
| LAU 331 | DRB1*0301/0701, DRB3*0101, DRB4*0101 | 31-50 | DR | DRB1*0301 |
| | | 51-70 | DR | DRB1*0701 |
| LAU 672 | DRB1*0301/1101, DRB3*0101-0202 | 31-50 | DR | DRB1*1101 |
| | | 61-80 | DR | DRB1*1101 |
| | | 101-120 | DR | DRB1*1101 |

The restricting MHC class II element was assessed in peptide presentation experiments in the presence of antibodies known to specifically block antigen recognition restricted by different MHC-class II element. The restricting allele was determined in peptide presentation experiments using homozygous EVB-B expressing each of the patient's alleles.

TABLE 3

Determination of the HLA class II presenting allele using molecularly typed APC

| LAU 331 31-50A | COX (+)B | BH (−) | 0MW (−) |
|---|---|---|---|
| DRB1*0301-0701 DRB3*0101 DRB4*0101 | DRB1*0301 DRB3*0101 | DRB1*0701 DRB4*0101 | DRB1*1301 DRB3*0101 |

| LAU 672 31-50 | COX (−) | JBUSH (+) | LAU 14 (+) | 0MW (−) | 31227ABO (−) |
|---|---|---|---|---|---|
| DRB1*0301-1101 DRB3*0101-0202 | DRB1*0301 DRB3*0101 | DRB1*1101 DRB3*0202 | DRB1*1101 DRB3*0202 | DRB1*1301 DRB3*0101 | DRB1*1401 DRB3*0202 |

| LAU 97 41-60 | 0MW (−) | SCHU (+) | COX (−) |
|---|---|---|---|
| DRB1*1301-1501 DRB3*0101 DRB5*0101 | DRB1*1301 DRB3*0101 | DRB1*1501 DRB5*0101 | DRB1*0301 DRB3*0101 |

| LAU 331 51-70 | COX (−) | BH (+) | 0MW (−) | T7526 (−) |
|---|---|---|---|---|
| DRB1*0301-0701 DRB3*0101 DRB4*0101 | DRB1*0301 DRB3*0101 | DRB1*0701 DRB4*0101 | DRB1*1301 DRB3*0101 | DRB1*0901 DRB4*0101 |

| LAU 672 61-80 | COX (−) | JBUSH (+) | 31227ABO (−) |
|---|---|---|---|
| DRB1*0301-1101 DRB3*0101-0202 | DRB1*0301 DRB3*0101 | DRB1*1101 DRB3*0202 | DRB1*1401 DRB3*0202 |

| LAU 672 101-120 | COX (−) | JBUSH (+) | 31227ABO (−) |
|---|---|---|---|
| DRB1*0301-1101 DRB3*0101-0202 | DRB1*0301 DRB3*0101 | DRB1*1101 DRB3*0202 | DRB1*1401 DRB3*0202 |

| LAU 14 101-120 | JBUSH (+) | 31227ABO (−) |
|---|---|---|
| DRB1*1101 DRB3*0202 | DRB1*1101 DRB3*0202 | DRB1*1401 DRB3*0202 |

| LAU 97 151-170 | SCHU (−) | BM21 (+) |
|---|---|---|
| DPB1*0402/1001 | DPB1*0402 | DPB1*0101 |

[A] For each CD4+ T cell specificity tested the code of the corresponding patient and the reactive SSX-4 peptide are shown.
[B] The ability of peptide pulsed APC to present or not the appropriate peptide to the corresponding CD4+ T cell clones is indicated as (+) or (−).

Figure 3:
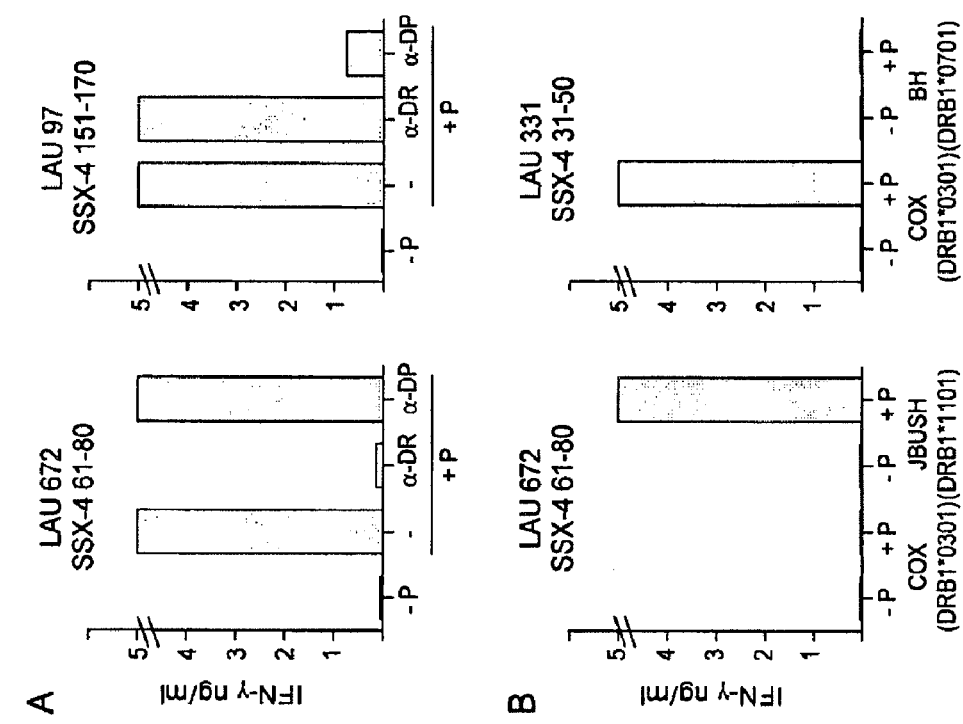
FIG. 3. Determination of the MHC class II restricting elements and alleles. (A) To determine the MHC class II restricting element, peptide recognition was assessed either in the absence or in the presence of anti HLA-DR or -DP antibodies. (B) The MHC class II restricting allele was determined by assessing the ability of molecularly typed EBV-B cells to present SSX-4 peptides to the corresponding CD4+ T cell clones.

Examples of these experiments are shown in FIG. 3. The results obtained for all clones are summarized above and in Table 3.

Recognition of Naturally Processed SSX-4 Antigen by Specific CD4+ T Cell Clones.

Figure 4:
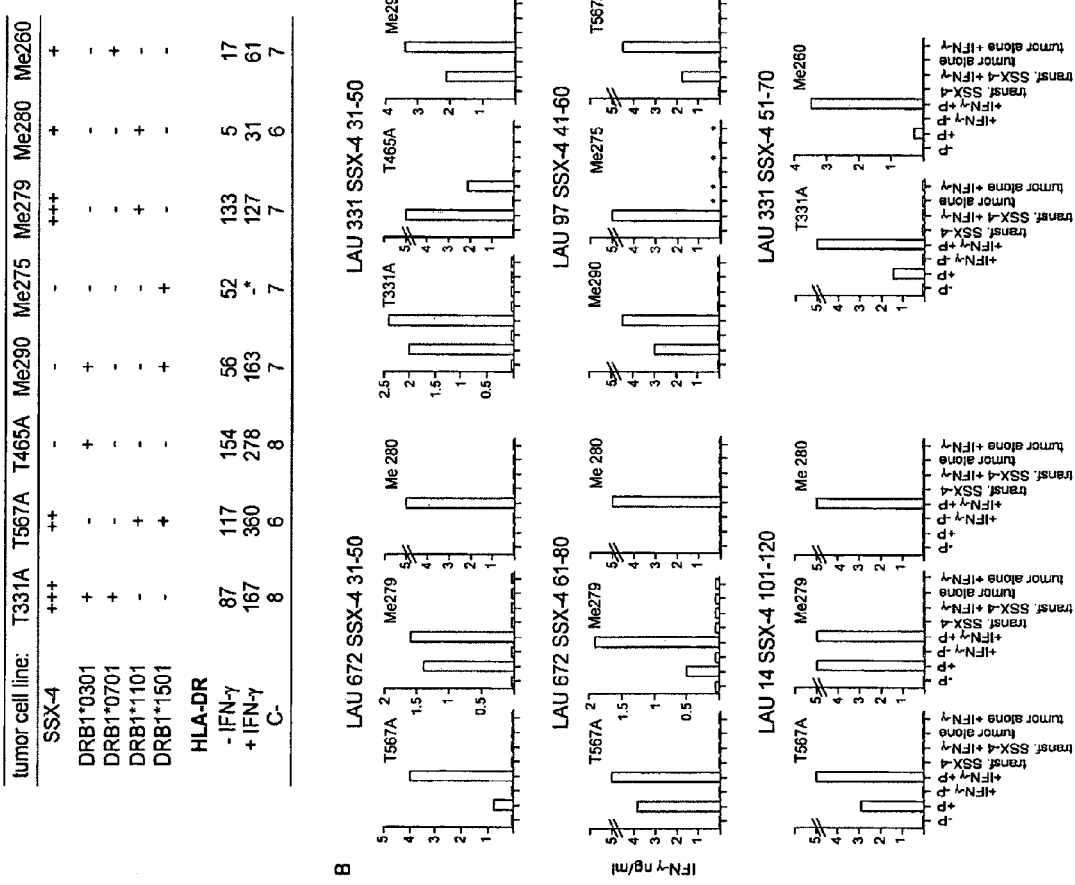
FIG. 4. Lack of recognition of endogenous SSX-4 antigen by specific CD4+ T cells. (A) Expression of SSX-4 in tumor lines was assessed by PCR. HLA-DR alleles were determined by molecular typing. Surface expression of HLA-DR was assessed using specific mAb. Where indicated, cells were treated with IFN-γ (200 IU/ml) during 24 h. (B) Recognition of melanoma cell lines, transfected or not with an SSX-4 encoding plasmid, after 24 hr incubation with SSX-4 specific CD4+ T cells, was assessed by ELISA measurement of IFN-γ secretion in the culture supernatant, in the absence, or in the presence of peptide. Where indicated, cells were treated with IFN-γ during 24 h and extensively washed prior to test. *Me275 cells died upon treatment with IFN-γ.
Figure 5:
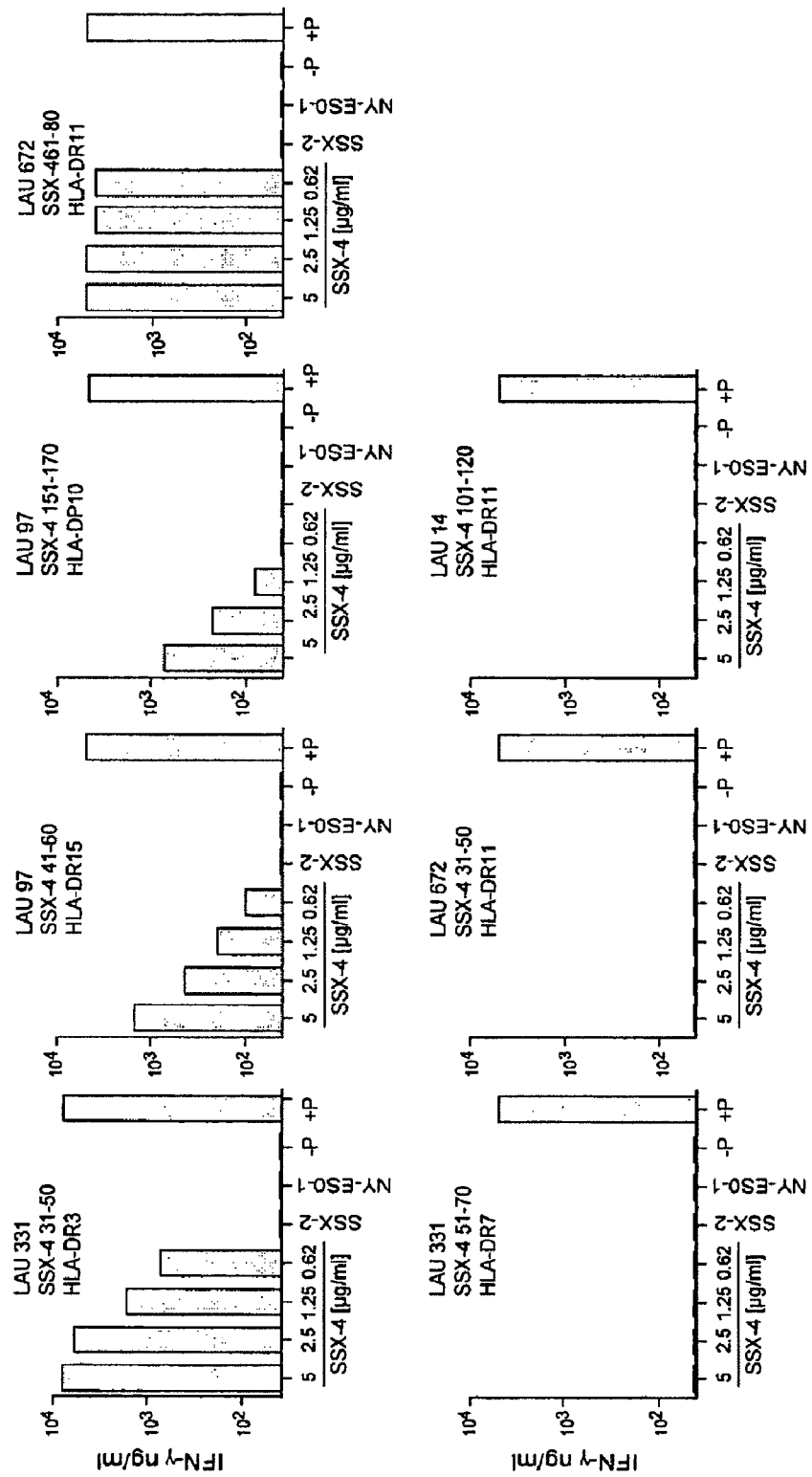
FIG. 5. Processing and presentation of recombinant SSX-4 protein to specific CD4+ T cells by professional APC. The ability of monocyte derived DC to process the SSX-4 protein and present the relevant epitopes to specific CD4+ T cells was assessed after 12 h incubation of DC with soluble recombinant SSX-4 protein, at the indicated dose. Recombinant SSX-2 and NY-ESO-1 proteins as well as the corresponding active peptide(s) were used as internal controls, as indicated.

To assess the recognition of endogenously expressed SSX-4 antigen by specific CD4+ T cells, we selected a panel of melanoma cell lines characterized in terms of expression of SSX-4, relevant MHC class II molecules and HLA-DR expression levels (FIG. 4A). All tumor cell lines, with the exception of Me280, expressed detectable levels of HLA-DR molecules at the cell surface. In addition for all cell lines, with the exception of Me279, HLA-DR expression was significantly enhanced after treatment with IFN-γ. Recognition of endogenous SSX-4 antigen by specific CD4+ T cells was assessed using the tumor cell lines as such or after treatment with IFN-γ and/or transfection with an SSX-4 encoding plasmid. Recognition of endogenous SSX-4 antigen by HLA-DP10 restricted CD4+ T cells could not be assessed because of unavailability of appropriate tumor cell lines. In all the other cases, however, tumor cells were not significantly recognized by SSX-4 specific CD4+ T cells, irrespectively of IFN-γ treatment, and transfection with SSX-4 encoding plasmid, unless the peptide was added exogenously (FIG. 4B). We then assessed the ability of professional APC to process the SSX-4 antigen and present the different epitopes to the corresponding CD4+ T cells. As illustrated in FIG. 5, monocyte derived dendritic cells (DC) were able to present the recombinant SSX-4 protein to specific CD4+ T cells in the case of the following epitopes: the DR3 restricted 31-50, the DR15 (or DRB5*0101) restricted 41-60, the DR11 restricted 61-80 and the DP10 restricted 151-170. In contrast, no significant recognition of the DR11 restricted 31-50 epitope, the DR7 restricted 51-70 epitope nor the DR11 restricted 101-120 epitope was obtained under these test conditions.

Discussion

Expression of SSX genes in adult human tissues shows a very restricted distribution being mainly found in testis and, at a much lower level, in thyroid tissue (Gure, A. O., et al., 1997, SSX: a multigene family with several members transcribed in normal testis and human cancer, *Int J Cancer,* 72:965-971; Tureci, O., et al., 1998, Expression of SSX genes in human tumors, *Int J Cancer,* 77:19-23). However, ectopic expression of SSX genes is detectable in variable proportions of tumors of different histological types. This expression pattern is typical of the so-called cancer/testis antigens (CTA) group (Scanlan, M. J., et al., 2002, Cancer/testis antigens: an expanding family of targets for cancer immunotherapy, *Immunol Rev,* 188:22-32), to which the SSX gene family belongs. Similarly to other CTA, SSX promoter activity is methylation sensitive, suggesting that CTA gene expression could be at least partially due to the genome-wide demethylation occurring in cancer (De Smet, C., et al., 1996, The activation of human gene MAGE-1 in tumor cells is correlated with genome-wide demethylation, *Proc Natl Acad Sci USA,* 93:7149-7153; De Smet, C., et al., 2004, Promoter-dependent mechanism leading to selective hypomethylation within the 5' region of gene MAGE-A1 in tumor cells, *Mol Cell Biol,* 24:4781-4790). In addition, expression of SSX genes can occur as a result of the chromosomal translocations t(X;18)(p11.2;q11.2) commonly found in synovial sarcoma, representing, in some cases, the only detectable cytogenetic abnormality (Sandberg, A. A., and Bridge, J. A., 2002, Updates on the cytogenetics and molecular genetics of bone and soft tissue tumors. Synovial sarcoma, *Cancer Genet Cytogenet,* 133:1-23). The translocation involves the SYT gene, which is ubiquitously expressed and functions as an activator of transcription and SSX-1 or -2 and, less frequently, SSX-4 (Brodin, B., et al., 2001, Cloning and characterization of spliced fusion transcript variants of synovial sarcoma: SYT/SSX4, SYT/SSX4v, and SYT/SSX2v. Possible regulatory role of the fusion gene product in wild type SYT expression, *Gene,* 268:173-182). The predicted SSX gene products are 188 amino acids long proteins sharing 70 to 90% homology. SSX proteins are rich in arginine and lysine and contain consensus sequences for both N-glycosilation and tyrosine phosphorylation (Crew, A. J., et al., 1995, Fusion of SYT to two genes, SSX1 and SSX2, encoding proteins with homology to the Kruppel-associated box in human synovial sarcoma, *Embo J,* 14:2333-2340). Their sequence is characterized by three nuclear localization signals (dos Santos, N. R., et al., 1997, Nuclear localization of SYT, SSX and the synovial sarcoma-associated SYT-SSX fusion proteins, *Hum Mol Genet,* 6:1549-1558), an N-terminal region with homology to the Kruppel-associated box (KRAB) domain (subdivided into two subdomains, A and B) predicted to form two amphipathic helices, and a highly conserved acidic C-terminal domain (SSXRD). Despite these striking features, to date, little is known about the normal biological function of SSX genes products.

Several lines of evidence, however, consistent with their localization to the cell nucleus, point at their role as modulators of gene transcription. Transcriptional repression activity has been initially reported for the full-length SSX-1 and attributed to the KRAB domain (Brett, D., et al., 1997, The SYT protein involved in the t(X;18) synovial sarcoma translocation is a transcriptional activator localised in nuclear bodies, *Hum Mol Genet,* 6:1559-1564). Subsequent studies by Lim F L et al. (1998, A KRAB-related domain and a novel transcription repression domain in proteins encoded by SSX genes that are disrupted in human sarcomas, *Oncogene,* 17:2013-2018), however, have shown that the SSX-1(–2) KRAB domains have a highly decreased capacity of down-modulating the trans-activation of a reporter gene, as compared to a previously characterized KRAB repression domain (Margolin, J. F., et al., 1994, Kruppel-associated boxes are potent transcriptional repression domains, *Proc Natl Acad Sci USA,* 91:4509-4513) due to their inability to interact with the co-repressor TIF1β (Moosmann, P., et al., 1996, Transcriptional repression by RING finger protein TIF1 beta that interacts with the KRAB repressor domain of KOX1, *Nucleic Acids Res.,* 24:4859-4867). The same study has identified the SSXRD domain as the main SSX-1 repressor domain of functional significance. Location of the actual repressor domain at the C-terminus of SSX (that is retained in the SYT-SSX fusion proteins) explains the decreased ability of SYT-SSX2 to activate transcription as compared to unrearranged SYT and could help understanding the impact of expression of both SYT-SSX and full-length SSX antigens in neoplasia. Together, the current information about expression and activity of the SSX gene products converges towards an important role played by these molecules in cancer and supports their interest as targets for immunotherapy of cancer.

SSX-4 is among the SSX genes most frequently expressed in tumors of different histological types (Tureci, O., et al., 1998, Expression of SSX genes in human tumors, *Int J Cancer,* 77:19-23; Naka, N., et al., 2002, Expression of SSX genes in human osteosarcomas, *Int J Cancer,* 98:640-642; Ayyoub, M., et al., 2003, SSX antigens as tumor vaccine targets in human sarcoma, *Cancer Immunity,* 3:13). Phylogenetically, it is less closely related to the other family members (Gure, A. O., et al., 2002, The SSX gene family: Characterization of 9 complete genes, *Int J Cancer,* 101:448-453). Dos Santos N R and colleagues have generated a mouse anti-human SSX mAb using an SSX-2 recombinant protein as immunogen (dos Santos, N. R., et al., 1997, Nuclear localization of SYT, SSX and the synovial sarcoma-associated SYT-SSX fusion proteins, *Hum Mol Genet,* 6:1549-1558). The antibody (E3AS) cross-recognizes SSX-4 and is able to detect the antigen in the nucleus of HeLa cells transfected with a SSX-4 expression construct, thus confirming the nuclear localization of the SSX-4 antigen. Interestingly, a recent study has identified two SSX-2 interacting proteins (RAB3IP and SSX2IP). Both of them, however, failed to show any significant interaction with SSX-4, indicating that, despite their homology, these proteins likely perform different functions (de Bruijn, D. R., et al., 2002, The cancer-related protein SSX2 interacts with the human homologue of a Ras-like GTPase interactor, RAB3IP, and a novel nuclear protein, SSX2IP, *Genes Chromosomes Cancer,* 34:285-298).

The immunogenicity of SSX-4 had not been addressed prior to this study. We undertook the assessment of natural CD4$^+$ T cell responses to the SSX-4 antigen in melanoma patients bearing antigen-expressing tumors as part of a larger project aimed at the development of SSX-based immunotherapy in cancer patients. The essential role of tumor antigen specific CD4$^+$ T cells in immune response to tumors has lately been fully acknowledged (Toes, R. E., et al., 1999, CD4 T cells and their role in antitumor immune responses, *J Exp Med,* 189:753-756). Tumor antigen specific CD4$^+$ T cells have been shown to mediate antitumor immune responses through a variety of different mechanisms. They participate in the effector phase of tumor rejection both indirectly via macrophage/eosinophil activation and by producing inflammatory cytokines such as IFN-γ, and sometimes through direct killing of tumor cells (James, R. F., et al., 1991, The effect of class II gene transfection on the tumourigenicity of the H-2K-negative mouse leukaemia cell line K36.16, *Immunology,* 72:213-218; Hung, K., et al., 1998, The central role of CD4(+) T cells in the antitumor immune response, *J Exp Med,* 188:2357-2368; Mumberg, D., et al., 1999, CD4(+) T cells eliminate MHC class II-negative cancer cells in vivo by indirect effects of IFN-gamma, *Proc Natl Acad Sci USA,* 96:8633-8638; Old, L. J., 1996, Immunotherapy for cancer, *Sci Am,* 275:136-143; Qin, Z., and Blankenstein, T., 2000, CD4+ T cell-mediated tumor rejection involves inhibition of angiogenesis that is dependent on IFN gamma receptor expression by nonhematopoietic cells, *Immunity,* 12:677-686). In addition and importantly they exert helper functions for priming and maintenance of tumor antigen specific CD8$^+$ T cells (Toes, R. E., et al., 1999, CD4 T cells and their role in antitumor immune responses, *J Exp Med,* 189: 753-756; Wang, R. F., 2001, The role of MHC class II-restricted tumor antigens and CD4+ T cells in antitumor immunity, *Trends Immunol,* 22:269-276) and for production of tumor antigen specific antibodies (Glennie, M. J., and Johnson, P. W., 2000, Clinical trials of antibody therapy, *Immunol Today,* 21:403-410; Greenberg, P. D., 1991, Adoptive T cell therapy of tumors: mechanisms operative in the recognition and elimination of tumor cells, *Adv Immunol,* 49:281-355). Assessment of natural CD4$^+$ T cell responses to tumor antigens and identification of tumor antigen derived sequences recognized by CD4$^+$ T cells in association with frequently expressed MHC class II alleles are, therefore, important elements for the implementation of cancer immunotherapy.

The analysis of tumor antigen specific CD4$^+$ T cells has proven difficult mainly because of the lack of appropriate methodological approaches for their detection and isolation, further complicated by their generally low ex vivo frequency that hampers their direct analysis (Klenerman, P., et al., 2002, Tracking T cells with tetramers: new tales from new tools, *Nat Rev Immunol,* 2:263-272; Kwok, W. W., et al., 2002, Use of class II tetramers for identification of CD4+ T cells, *J Immunol Methods,* 268:71-81). Several approaches have been developed, some successfully, including elution of MHC class II bound peptides from tumor cells (Halder, T., et al., 1997, Isolation of novel HLA-DR restricted potential tumor-associated antigens from the melanoma cell line FM3, *Cancer Res,* 57:3238-3244), peptide purification from tumor cell lysates (Pieper, R., et al., 1999, Biochemical identification of a mutated human melanoma antigen recognized by CD4(+) T cells, *J Exp Med,* 189:757-766) or artificial targeting of tumor antigens to the endogenous antigen presentation pathway (Wang, R. F., et al., 1999, Cloning genes encoding MHC class II-restricted antigens: mutated CDC27 as a tumor antigen, *Science,* 284:1351-1354). Other approaches are also used based on MHC class II epitope prediction algorithms (Rammensee, H., et al., 1999, SYFPEITHI: database for MHC ligands and peptide motifs, *Immunogenetics,* 50:213-219; Sturniolo, T., et al., 1999, Generation of tissue-specific and promiscuous HLA ligand databases using DNA microarrays and virtual HLA class II matrices, *Nat Biotechnol,* 17:555-561).

We analyzed SSX-4 specific CD4$^+$ T cell responses in patients bearing antigen-expressing tumors, using a panel of 20 amino acid long peptides spanning the entire SSX-4 sequence. This approach offers several advantages over the ones mentioned above, as it is not technically cumbersome, allows the identification of CD4$^+$ T cell epitopes irrespective of their physiologic processing pathways, and leads to a comprehensive assessment of the immunogenicity of the overall antigen. To minimize the risk that relevant epitopes would be missed because present at the break points between the different peptides, peptides in the panel were designed overlapping by ten amino acids. This was feasible in the case of SSX-4 because of the relatively small size of the antigenic product. The peptides were used as a pool for in vitro stimulation of purified circulating CD4$^+$ T cells using cells from the CD4" fraction as APC, and for a first screening of the elicited responses. After one cycle of in vitro stimulation, responses to the peptide pool were detected in 3/4 patients and, after a second cycle, in 4/4 patients and none of the healthy donors. Therefore, this simple method was sensitive enough for the detection of in vivo primed CD4$^+$ T cells and did not apparently result in in vitro priming. Single peptides in the pool were then used to define individual activities. This analysis revealed a potential limitation of the method, due to peptide competition for binding to the MHC molecule, that is likely to occur also in the in vitro stimulation phase, but could be overcome by stimulating T cells with a mixture of APC incubated with single peptides from the pool.

For each of the detected specificities, CD4$^+$ T cell were isolated and cloned. Generation and maintenance of clonal populations is somewhat laborious but indispensable to unambiguously assess antigen specific T cells especially when using allogeneic APC. We identified 7 distinct epitopes, 6 of which were restricted by HLA-DR. HLA-DR molecules account for more than 90% of the HLA class II isotypes expressed on APC, the HLA-DRB1 locus being highly polymorphic. The majority of the identified epitopes, however, were restricted by HLA-DR alleles frequently expressed in major ethnic groups. Three epitopes were restricted by DR11 (17% of Caucasians, 18.1% of Blacks, 4.9% of Japanese, 19.4% of Chinese, 18.1% of Hispanics) one by DRB3 (17.7% of Caucasians, 19.5% of Blacks, 0.4% of Japanese, 7.3% of Chinese, 14.4% of Hispanics) one by DR7 (26.2% of Caucasians, 11.1% of Blacks, 1% of Japanese, 15% of Chinese, 16.6% of Hispanics) and one by DRB15 (19.9% of Caucasians, 14.8% of Blacks, 30.9% of Japanese, 22% of Chinese, 15.0% Hispanic) (1991, *The Data Book of the 11th International Histocompatibility Workshop*, Yokohama, 807-814 pp).

We also identified an epitope restricted by HLA-DP10, which is less frequently expressed (2.2% of French, 1.6% of Canadians) (1991, *The Data Book of the 11th International Histocompatibility Workshop*, Yokohama, 807-814 pp). HLA-DP molecules have been generally scarcely studied. Recently, however, HLA-DP tumor-antigen derived T cell epitopes have been described (Schultz, E. S., et al., 2000, A MAGE-A3 peptide presented by HLA-DP4 is recognized on tumor cells by CD4+ cytolytic T lymphocytes, *Cancer Res*, 60:6272-6275; Zeng, G., et al., 2001, CD4(+) T cell recognition of MHC class II-restricted epitopes from NY-ESO-1 presented by a prevalent HLA DP4 allele: association with NY-ESO-1 antibody production, *Proc Natl Acad Sci USA*, 98:3964-3969). HLA-DP molecules have been previously shown to present peptides derived from infectious agents and alloantigens (Gaschet, J., et al., 1996, Acute graft versus host disease due to T lymphocytes recognizing a single HLA-DPB1*0501 mismatch, *J Clin Invest*, 98:100-107; Stephens, H. A., et al., 1995, The presence of the HLA class II allele DPB1*0501 in ethnic Thais correlates with an enhanced vaccine-induced antibody response to a malaria sporozoite antigen, *Eur J Immunol*, 25:3142-3147). It has also been suggested that some HLA-DP alleles may play a role in autoimmune diseases such as juvenile chronic arthritis (Murray, K. J., et al., 1999, Age-specific effects of juvenile rheumatoid arthritis-associated HLA alleles, *Arthritis Rheum*, 42:1843-1853). The functional role of HLA-DP (and HLA-DQ) molecules in the immune response, however, in relation to that of HLA-DR, is still unclear and subject to investigation.

Figure 6:
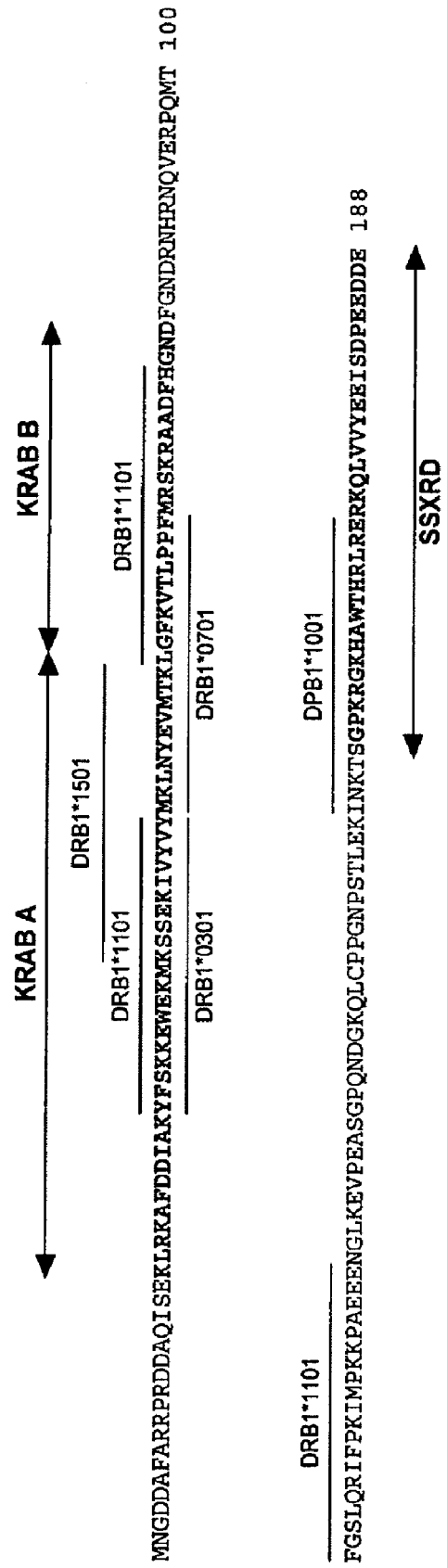
FIG. 6. Epitope distribution in the SSX-4 sequence. Location of the previously described KRAB domain (divided in the A and B subdomains) and the SSXRD domain are to indicated. For each epitope, both the location of the SSX-4 peptide (SEQ ID NO:1) used for its identification as well as the corresponding restricting allele are indicated.

Five of the seven epitopes identified in this study are localized in the KRAB domain of SSX-4 (FIG. 6). Interestingly, the 4 previously defined SSX-2 T cell epitopes (Ayyoub, M., et al., 2002, Proteasome-assisted identification of a SSX-2-derived epitope recognized by tumor-reactive CTL infiltrating metastatic melanoma, *J Immunol*, 168:1717-1722; Ayyoub, M., et al., 2004, Identification of an SSX-2 epitope presented by dendritic cells to circulating autologous CD4+ T cells, *J Immunol*, 172:7206-7211; Ayyoub, M., et al., 2004, An immunodominant SSX-2-derived epitope recognized by CD4+ T cells in association with HLA-DR, *J Clin Invest*, 113:1225-1233) (and manuscript submitted for publication) are also located in the KRAB domain. Previous studies have indicated that the immunogenicity of antigenic sequences can be influenced by their location within defined protein stretches, most likely because of their accessibility to fragmentation by proteases in the antigen processing pathway (Surman, S., et al., 2001, Localization of CD4+ T cell epitope hotspots to exposed strands of HIV envelope glycoprotein suggests structural influences on antigen processing, *Proc Natl Acad Sci USA*, 98:4587-4592). Therefore, although structural data on SSX proteins are not yet available, our findings suggest that the KRAB domain could be particularly exposed to degradation by proteases resulting in a "hot spot" region for T cell recognition.

CD4+ T cells specific for 6 of the 7 epitopes (the DP10 restricted epitope could not be evaluated because of lack of DP10 expressing targets) failed to recognize endogenously expressed SSX-4 antigen. Similar results were previously obtained for SSX-2 reactive CD4+ T cells specific of 3 distinct epitopes (Ayyoub, M., et al., 2004, Identification of an SSX-2 epitope presented by dendritic cells to circulating autologous CD4+ T cells, *J Immunol*, 172:7206-7211; Ayyoub, M., et al., 2004, An immunodominant SSX-2-derived epitope recognized by CD4+ T cells in association with HLA-DR, *J Clin Invest*, 113:1225-1233) (and manuscript submitted for publication). In the case of other CTA (MAGE-A3 and NY-ESO-1), both CD4+ T cell epitopes presented or not through the endogenous pathway have been described (Schultz, E. S., et al., 2000, A MAGE-A3 peptide presented by HLA-DP4 is recognized on tumor cells by CD4+ cytolytic T lymphocytes, *Cancer Res*, 60:6272-6275; Zeng, G., et al., 2001, CD4(+) T cell recognition of MHC class II-restricted epitopes from NY-ESO-1 presented by a prevalent HLA DP4 allele: association with NY-ESO-1 antibody production, *Proc Natl Acad Sci USA*, 98:3964-3969; Chaux, P., et al., 1999, Identification of MAGE-3 epitopes presented by HLA-DR molecules to CD4(+) T lymphocytes, *J Exp Med*, 189:767-778). It is, however, noteworthy that both MAGE-A3 and NY-ESO-1 are cytoplasmic antigens (Kocher, T., et al., 1995, Identification and intracellular location of MAGE-3 gene product, *Cancer Res*, 55:2236-2239; Schultz-Thater, E., et al., 2000, NY-ESO-1 tumour associated antigen is a cytoplasmic protein detectable by specific monoclonal antibodies in cell lines and clinical specimens, *Br J Cancer*, 83:204-208). In contrast, the nuclear localization of SSX proteins during most of the cell cycle (dos Santos, N. R., et al., 1997, Nuclear localization of SYT, SSX and the synovial sarcoma-associated SYT-SSX fusion proteins, *Hum Mol Genet*, 6:1549-1558; dos Santos, N. R., et al., 2000, Heterogeneous expression of the SSX cancer/testis antigens in human melanoma lesions and cell lines, *Cancer Res*, 60:1654-1662), could hamper their accessibility to the MHC class II endogenous processing pathway. Direct recognition of tumor cells is probably not the dominant mechanism through which tumor antigen-specific CD4+ T cells contribute to tumor rejection in vivo (Toes, R. E., et al., 1999, CD4 T cells and their role in antitumor immune responses, *J Exp Med*, 189:753-756; Hung, K., et al., 1998, The central role of CD4(+) T cells in the antitumor immune response, *J Exp Med*, 188:2357-2368; Wang, R. F., 2001, The role of MHC class II-restricted tumor antigens and CD4+ T cells in antitumor immunity, *Trends Immunol*, 22:269-276). Therefore, lack of recognition of endogenous SSX antigens by specific CD4+ T cells does not imply a lesser role of these cells in the immune response to SSX antigen-expressing tumors.

Lack of recognition of endogenous SSX antigens by specific CD4+ T cells indicates that their in vivo processing and presentation mainly occur through the exogenous pathway. In support of this, 4 of the 7 identified SSX-4 epitopes were efficiently processed and presented to specific CD4+ T cells upon incubation of monocyte derived dendritic cells with SSX-4 recombinant protein. In contrast, the 3 remaining epitopes were not significantly presented under identical test conditions. Although it cannot formally be excluded that the SSX-4 peptide reactive CD4+ T cells that failed to recognize the native antigen were isolated because of the homology between the SSX-4 peptides with a putative unrelated antigen, this explanation seems unlikely, as no response to any of the SSX-4 peptides was detected in healthy donors. A more likely possibility is that these CD4+ T cells recognize "cryptic" epitopes that are presented after the exposure to the antigen in peptide form but not after processing of the whole protein antigen under our test conditions (Sercarz, E. E., et al., 1993, Dominance and crypticity of T cell antigenic determinants, *Annu. Rev. Immunol.*, 11:729-766). Previous studies have indicated that both the nature of APC and/or the presence of soluble factors can alter the repertoire of naturally processed epitopes available for T cell recognition (Drakesmith, H., et al., 1998, In vivo priming of T cells against cryptic determinants by dendritic cells exposed to interleukin 6 and native antigen, *Proc Natl Acad Sci USA*, 95:14903-14908; Nanda, N. K., and Sant, A. J., 2000, DM determines the cryptic and immunodominant fate of T cell epitopes, *J Exp Med*, 192:781-788; Viner, N. J., et al., 1995, Identification of a major I-Ek-restricted determinant of hen egg lysozyme: limitations of lymph node proliferation studies in defining immunodominance and crypticity, *Proc Natl Acad Sci USA*, 92:2214-2218). Retrieval of responses to SSX-4 "cryptic" epitopes in patients bearing antigen expressing tumors strongly suggests that priming of these CD4+ T cells has occurred in vivo, possibly under inflammatory conditions and/or by APC distinct from those used in our test conditions.

In conclusion, the results of this study demonstrate that the SSX-4 encoded antigen is spontaneously immunogenic, supporting its use for implementation of SSX-based immunotherapy of cancer. By analyzing SSX-4 specific CD4+ T cell responses in melanoma patients, we have identified seven distinct CD4+ T cell epitopes target of spontaneous responses in antigen expressing patients. The identified epitopes were mostly presented in association with frequently expressed alleles that collectively cover 35-80% of individuals from several major ethnic groups. The majority of the epitopes were located in the KRAB domain suggesting a dominant role of this region of the protein in the induction of SSX specific immune responses. Together, these findings will be highly instrumental for the onset and monitoring of SSX based immunotherapy trials.

Other aspects of the invention will be clear to the skilled artisan and need not be repeated here. Each reference cited herein is incorporated by reference in its entirety.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nucleic acid molecule encoding an SSX-4 HLA class II-binding peptide, wherein the HLA class II-binding peptide comprises the amino acid sequence selected from the group consisting of SEQ ID NO:5, SEQ ID NO:6, SEQ ID NO:7, SEQ ID NO:8, and SEQ ID NO:9, and wherein the HLA class II-binding peptide does not include a full length SSX-4 protein as provided in SEQ ID NO: 1 or SEQ ID NO: 3.

2. The isolated nucleic acid molecule of claim 1, wherein the HLA class II-binding peptide consists of the amino acid sequence selected from the group consisting of SEQ ID NO:5, SEQ ID NO:6, SEQ ID NO:7, SEQ ID NO:8, SEQ ID NO:9, and SEQ ID NO:10.

3. The isolated nucleic acid molecule of claim 1, wherein the HLA class II-binding peptide comprises an endosomal targeting signal.

4. The isolated nucleic acid molecule of claim 3, wherein the endosomal targeting signal comprises an endosomal targeting portion of human invariant chain Ii.

5. An isolated nucleic acid molecule encoding an SSX-4 HLA class II-binding peptide, wherein the HLA class II-binding comprises the amino acid sequence of SEQ ID NO:10, and wherein the HLA class II-binding peptide comprises up to 188 amino acid residues and does not include (i) a full length SSX-4 protein as provided in SEQ ID NO: 1 or SEQ ID NO: 3, or (ii) a full-length SSX-7 protein.

6. The isolated nucleic acid molecule of claim 5, wherein the HLA class II-binding peptide comprises an endosomal targeting signal.

7. The isolated nucleic acid molecule of claim 6, wherein the endosomal targeting signal comprises an endosomal targeting portion of human invariant chain Ii.

8. An expression vector comprising the isolated nucleic acid molecule of any of claims 1-7 operably linked to a promoter.

9. The expression vector of claim 8, further comprising a nucleic acid molecule that encodes an HLA-DR molecule.

10. A host cell transfected or transformed with the expression vector of claim 8.

11. The host cell of claim 10, wherein the host cell expresses an HLA-DR molecule.

* * * * *

SEQUENCE LISTING

<160> NUMBER OF SEQ ID NOS: 10

<210> SEQ ID NO 1
<211> LENGTH: 188
<212> TYPE: PRT
<213> ORGANISM: Homo sapiens

<400> SEQUENCE: 1

```
Met Asn Gly Asp Asp Ala Phe Ala Arg Arg Pro Arg Asp Asp Ala Gln
1               5                   10                  15

Ile Ser Glu Lys Leu Arg Lys Ala Phe Asp Asp Ile Ala Lys Tyr Phe
            20                  25                  30

Ser Lys Lys Glu Trp Glu Lys Met Lys Ser Ser Glu Lys Ile Val Tyr
        35                  40                  45

Val Tyr Met Lys Leu Asn Tyr Glu Val Met Thr Lys Leu Gly Phe Lys
    50                  55                  60

Val Thr Leu Pro Pro Phe Met Arg Ser Lys Arg Ala Ala Asp Phe His
65                  70                  75                  80

Gly Asn Asp Phe Gly Asn Asp Arg Asn His Arg Asn Gln Val Glu Arg
                85                  90                  95

Pro Gln Met Thr Phe Gly Ser Leu Gln Arg Ile Phe Pro Lys Ile Met
            100                 105                 110

Pro Lys Lys Pro Ala Glu Glu Glu Asn Gly Leu Lys Glu Val Pro Glu
        115                 120                 125

Ala Ser Gly Pro Gln Asn Asp Gly Lys Gln Leu Cys Pro Pro Gly Asn
    130                 135                 140

Pro Ser Thr Leu Glu Lys Ile Asn Lys Thr Ser Gly Pro Lys Arg Gly
145                 150                 155                 160

Lys His Ala Trp Thr His Arg Leu Arg Glu Arg Lys Gln Leu Val Val
                165                 170                 175

Tyr Glu Glu Ile Ser Asp Pro Glu Glu Asp Asp Glu
            180                 185
```

<210> SEQ ID NO 2
<211> LENGTH: 1250
<212> TYPE: DNA
<213> ORGANISM: Homo sapiens

<400> SEQUENCE: 2

-continued

```
acacgccgat tgcccttttt gattcttcca caatcagggt gagactgctc ccagtgccat      60
gaacggagac gacgcctttg caaggagacc cagggatgat gctcaaatat cagagaagtt     120
acgaaaggcc ttcgatgata ttgccaaata cttctctaag aaagagtggg aaaagatgaa     180
atcctcggag aaaatcgtct atgtgtatat gaagctaaac tatgaggtca tgactaaact     240
aggtttcaag gtcaccctcc cacctttcat gcgtagtaaa cgggctgcag acttccacgg     300
gaatgatttt ggtaacgatc gaaaccacag gaatcaggtt gaacgtcctc agatgacttt     360
cggcagcctc cagagaatct tcccgaagat catgcccaag aagccagcag aggaagaaaa     420
tggtttgaag gaagtgccag aggcatctgg cccacaaaat gatgggaaac agctgtgccc     480
cccgggaaat ccaagtacct tggagaagat taacaagaca tctggaccca aaggggggaa     540
acatgcctgg acccacagac tgcgtgagag aaagcagctg gtggtttatg aagagatcag     600
cgaccctgag gaagatgacg agtaactccc ctcggggata tgacacatgc ccatgatgag     660
aagcagaacg tggtgacctt tcacgaacat gggcatggct gcggacccct cgtcatcagg     720
tgcatagcaa gtgaaagcaa gtgttcacaa cagtgaaaag ttgagcgtca ttttcttag      780
tgtgccaaga gttcgatgtt ggcgtttccg ctgtattttc ttgcagtgtg ccattctgtt     840
agacattagc gttttcgttg atgagcaaga catgcttaat gcatatttcg cttgtgtat     900
ccatgcacct acctcagaaa acaagtattg tcaggtattc tctccataga acagcactac     960
cctcctctct ccccagatgt gactactgag gggaggtctg agtgtttaat ttccgatttt    1020
ttcctctgca tttacacaca caccacacac gcacacacac acaccaagta ccagtataag    1080
catctcccat ctgctttctc ccattgccat gcgacctggt caagcccccc tcactctgtt    1140
tcctgttcag catgtactcc cctcatccga ttccgttgta tcagtcactg acagttaata    1200
aacctttgca aacgttcaaa aaaaaaaaaa aaaaaaaaaa aaaaaaaaa              1250
```

<210> SEQ ID NO 3
<211> LENGTH: 153
<212> TYPE: PRT
<213> ORGANISM: Homo sapiens

<400> SEQUENCE: 3

```
Met Asn Gly Asp Asp Ala Phe Ala Arg Arg Pro Arg Asp Asp Ala Gln
1               5                   10                  15

Ile Ser Glu Lys Leu Arg Lys Ala Phe Asp Asp Ile Ala Lys Tyr Phe
                20                  25                  30

Ser Lys Lys Glu Trp Glu Lys Met Lys Ser Ser Glu Lys Ile Val Tyr
            35                  40                  45

Val Tyr Met Lys Leu Asn Tyr Glu Val Met Thr Lys Leu Gly Phe Lys
 50                  55                  60

Val Thr Leu Pro Pro Phe Met Arg Ser Lys Arg Ala Ala Asp Phe His
 65                  70                  75                  80

Gly Asn Asp Phe Gly Asn Asp Arg Asn His Arg Asn Gln Val Glu Arg
                85                  90                  95

Pro Gln Met Thr Phe Gly Ser Leu Gln Arg Ile Phe Pro Lys Asp Pro
            100                 105                 110

Lys Gly Gly Asn Met Pro Gly Pro Thr Asp Cys Val Arg Glu Ser Ser
        115                 120                 125

Trp Trp Phe Met Lys Arg Ser Ala Thr Leu Arg Lys Met Thr Ser Asn
130                 135                 140

Ser Pro Arg Gly Tyr Asp Thr Cys Pro
145                 150
```

```
<210> SEQ ID NO 4
<211> LENGTH: 1114
<212> TYPE: DNA
<213> ORGANISM: Homo sapiens

<400> SEQUENCE: 4
acacgccgat tgccctttt gattcttcca caatcagggt gagactgctc ccagtgccat      60
gaacggagac gacgcctttg caaggagacc cagggatgat gctcaaatat cagagaagtt     120
acgaaaggcc ttcgatgata ttgccaaata cttctctaag aaagagtggg aaaagatgaa     180
atcctcggag aaaatcgtct atgtgtatat gaagctaaac tatgaggtca tgactaaact     240
aggtttcaag gtcaccctcc cacctttcat gcgtagtaaa cgggctgcag acttccacgg     300
gaatgatttt ggtaacgatc gaaaccacag gaatcaggtt gaacgtcctc agatgacttt     360
cggcagcctc cagagaatct tcccgaagga cccaaaaggg ggaaacatgc ctggacccac     420
agactgcgtg agagaaagca gctggtggtt tatgaagaga tcagcgaccc tgaggaagat     480
gacgagtaac tcccctcggg gatatgacac atgcccatga tgagaagcag aacgtggtga     540
cctttcacga acatgggcat ggctgcggac ccctcgtcat caggtgcata gcaagtgaaa     600
gcaagtgttc acaacagtga aaagttgagc gtcattttc ttagtgtgcc aagagttcga     660
tgttggcgtt tccgctgtat tttcttgcag tgtgccattc tgttagacat tagcgttttc     720
gttgatgagc aagacatgct taatgcatat ttcggcttgt gtatccatgc acctacctca     780
gaaaacaagt attgtcaggt attctctcca tagaacagca ctaccctcct ctctccccag     840
atgtgactac tgaggggagg tctgagtgtt taatttccga ttttttcctc tgcatttaca     900
cacacaccac acacgcacac acacacacca agtaccagta taagcatctc ccatctgctt     960
ttctccattg ccatgcgacc tggtcaagcc ccctcactc tgtttcctgt tcagcatgta    1020
ctcccctcat ccgattccgt tgtatcagtc actgacagtt aataaacctt tgcaaacgtt    1080
caaaaaaaaa aaaaaaaaa aaaaaaaaaa aaaa                                  1114

<210> SEQ ID NO 5
<211> LENGTH: 20
<212> TYPE: PRT
<213> ORGANISM: Homo sapiens

<400> SEQUENCE: 5

Tyr Phe Ser Lys Lys Glu Trp Glu Lys Met Lys Ser Ser Glu Lys Ile
1               5                   10                  15
Val Tyr Val Tyr
            20

<210> SEQ ID NO 6
<211> LENGTH: 20
<212> TYPE: PRT
<213> ORGANISM: Homo sapiens

<400> SEQUENCE: 6

Lys Ser Ser Glu Lys Ile Val Tyr Val Tyr Met Lys Leu Asn Tyr Glu
1               5                   10                  15
Val Met Thr Lys
            20

<210> SEQ ID NO 7
<211> LENGTH: 20
<212> TYPE: PRT
<213> ORGANISM: Homo sapiens
```

```
<400> SEQUENCE: 7

Met Lys Leu Asn Tyr Glu Val Met Thr Lys Leu Gly Phe Lys Val Thr
1               5                   10                  15

Leu Pro Pro Phe
            20

<210> SEQ ID NO 8
<211> LENGTH: 20
<212> TYPE: PRT
<213> ORGANISM: Homo sapiens

<400> SEQUENCE: 8

Leu Gly Phe Lys Val Thr Leu Pro Pro Phe Met Arg Ser Lys Arg Ala
1               5                   10                  15

Ala Asp Phe His
            20

<210> SEQ ID NO 9
<211> LENGTH: 21
<212> TYPE: PRT
<213> ORGANISM: Homo sapiens

<400> SEQUENCE: 9

Phe Gly Ser Leu Gln Arg Ile Phe Pro Lys Ile Met Pro Lys Lys Pro
1               5                   10                  15

Ala Glu Glu Glu Asn
            20

<210> SEQ ID NO 10
<211> LENGTH: 20
<212> TYPE: PRT
<213> ORGANISM: Homo sapiens

<400> SEQUENCE: 10

Ile Asn Lys Thr Ser Gly Pro Lys Arg Gly Lys His Ala Trp Thr His
1               5                   10                  15

Arg Leu Arg Glu
            20
```